(12) United States Patent
Drew

(10) Patent No.: US 10,190,091 B2
(45) Date of Patent: Jan. 29, 2019

(54) METHODS OF CELL SEPARATION

(71) Applicant: CELLS4LIFE GROUP LLP, Burgess Hill, Sussex (GB)

(72) Inventor: Jeffrey Drew, Burgess Hill (GB)

(73) Assignee: CELLS 4 LIFE GROUP LLP, Burgess Hill (GB)

( * ) Notice: Subject to any disclaimer, the term of this patent is extended or adjusted under 35 U.S.C. 154(b) by 0 days.

(21) Appl. No.: 14/784,492

(22) PCT Filed: Apr. 15, 2014

(86) PCT No.: PCT/GB2014/051177
§ 371 (c)(1),
(2) Date: Oct. 14, 2015

(87) PCT Pub. No.: WO2014/170662
PCT Pub. Date: Oct. 23, 2014

(65) Prior Publication Data
US 2016/0053224 A1    Feb. 25, 2016

(30) Foreign Application Priority Data

Apr. 15, 2013 (GB) .................................. 1306810.1

(51) Int. Cl.
*C12N 5/00* (2006.01)
*C12N 5/078* (2010.01)
*A01N 1/02* (2006.01)

(52) U.S. Cl.
CPC ......... *C12N 5/0087* (2013.01); *A01N 1/0221* (2013.01); *C12N 5/0634* (2013.01); *C12N 5/0641* (2013.01); *C12N 2500/32* (2013.01); *C12N 2500/34* (2013.01); *C12N 2500/62* (2013.01)

(58) Field of Classification Search
CPC .. C12N 5/0087; C12N 5/0641; C12N 5/0634; C12N 2500/62; C12N 2500/32; C12N 2500/34; A01N 1/0221
See application file for complete search history.

(56) References Cited

U.S. PATENT DOCUMENTS

| | | | |
|---|---|---|---|
| 3,902,964 A | 9/1975 | Greenspan | |
| 4,004,975 A | 1/1977 | Lionetti et al. | |
| 4,111,199 A | 9/1978 | Djerassi | |
| 4,159,896 A | 7/1979 | Levine et al. | |
| 6,140,123 A | 10/2000 | Demetriou et al. | |
| 6,544,751 B1 | 4/2003 | Brandwein et al. | |
| 7,598,089 B2 | 10/2009 | Collins | |
| 2003/0035843 A1 | 2/2003 | Livesey et al. | |
| 2004/0096813 A1 | 5/2004 | Baust et al. | |
| 2006/0252054 A1 | 11/2006 | Lin et al. | |
| 2008/0176250 A1 | 7/2008 | Banks | |
| 2008/0182233 A1* | 7/2008 | Collins ................ | C12N 5/0087 435/2 |
| 2009/0081689 A1 | 3/2009 | Yamanishi et al. | |
| 2010/0047213 A1 | 2/2010 | Zeitlin et al. | |
| 2010/0151438 A1 | 6/2010 | Yu et al. | |
| 2013/0059286 A1 | 3/2013 | Chang et al. | |

FOREIGN PATENT DOCUMENTS

| | | |
|---|---|---|
| CN | 102337245 A | 2/2012 |
| CN | 102758259 | 10/2012 |
| CN | 102960334 A | 3/2013 |
| EP | 0844482 A2 | 5/1998 |
| EP | 1683857 A1 | 7/2006 |
| EP | 2644689 A1 | 10/2013 |
| JP | 2000-201672 A | 7/2000 |
| WO | 94/25135 A1 | 11/1994 |
| WO | 95/10291 A1 | 4/1995 |
| WO | 2000/060351 A1 | 10/2000 |
| WO | 2003/031938 A2 | 4/2003 |
| WO | 2003/050536 A2 | 6/2003 |
| WO | 2007/092028 A2 | 8/2007 |
| WO | 2008/092014 A1 | 7/2008 |
| WO | 2010/021714 A2 | 2/2010 |
| WO | 2010/064973 A1 | 6/2010 |
| WO | 2012/061291 A2 | 5/2012 |

OTHER PUBLICATIONS

Wang et al. Incorporation of DMSO and dextran-40 into a gelatin/alginate hydrogel for controlled assembled cell cryopreservation. Cryobiology 61 (2010) 345-351.*
Klein et al. A Simple Method for the Separation of Leukocytes From Whole Blood. 1958. Am. J. Clin. Pathol. vol. 29. p. 550-552.*
Zeta Potential. 2007, downloaded from https://web.archive.org/web/20070208102740/https://msu.edu/~honda/zeta.htm. p. 1 (Year: 2007).*
Search Report for GB1306810.1 dated Jun. 25, 2014, 5 pages.
Search Report for GB1406768.0 dated Dec. 18, 2014, 5 pages.
International Search Report and Written Opinion for PCT/GB2014/051177 dated Jul. 16, 2014, 10 pages.
Armstrong et al., "The hydrodynamic radii of macromolecules and their effect on red blood cell aggregation", Biophys J. Dec. 2004, 87(6), 4259-70.
Branch et al., "Hematopoietic progenitor cells are resistant to dimethyl sulfoxide toxicity", Transfusion, Oct. 1994, 34(10), 887-90.
Clinical and Laboratory Standards Institute (CLSI). Enumeration of Immunologically Defined Cell Populations by Flow Cytometry; Approved Guideline—Second Edition. CLSI document H42-A2, May 2007, vol. 27, No. 16, 88 pages.

(Continued)

*Primary Examiner* — Taeyoon Kim
(74) *Attorney, Agent, or Firm* — Kilpatrick Townsend & Stockton LLP

(57) ABSTRACT

The present invention relates to the use of a combination of: (i) a macromolecular erythrocyte sedimentation enhancer, and (ii) dimethyl sulphoxide (DMSO), dimethylglycine (DMG) and/or valine; to recover non-erythrocyte blood cells from a blood cell-containing sample and/or to prime non-erythrocyte blood cells to protect their integrity in subsequent cryopreservation step(s).

26 Claims, 9 Drawing Sheets

(56) References Cited

OTHER PUBLICATIONS

Collins, "Cytokine and cytokine receptor expression as a biological indicator of immune activation: important considerations in the development of in vitro model systems", Sep. 2000, J Immunol Methods 243:125 (2000).
Fowke et al., Journal of Immunological Methods, 2000, 244, 139-144.
Hudspeth et al., "Improved post-thaw umbilical cord blood cell recovery vs. DMSO/Dextran," extracted from biolifesolutions.com website, Sep 4, 2014, 2 pages.
Huggins, CE, "Preservation of blood by freezing with dimethyl sulfoxide and its removal by dilution and erythrocyte agglomeration," Vox Sang 8:99-100, 1963.
Knöchel and Tiedemann, "Size distribution and cell-free translation of globin-coding HnRNA from avian erythroblasts", Biochim Biophys Acta, Feb. 10, 1975, 378(3), 383-93.
Lilford and Holt, "In vitro uses of biological cryoprotectants." Phil. Trans. R. Soc, Lond. B 2002, 357, 945-951.
Mantri S, Kanungo S and P. C. Mohapatra P. C., "Cryoprotective effect of disaccharides on cord blood stem cells with minimal use of DMSO", Indian Journal of Hematology and Blood Transfusion, Apr.-Jun. 2015 31(2), 206-212 (first online Feb. 23, 2014, 1-7).
Muralidharan, Tateishi and Maeda, "Simultaneous influence of erythrocyte deformability and macromolecules in the medium on erythrocyte aggregation: a kinetic study by a laser scattering technique", Biochim Biophys Acta, Sep. 1994, 1194(2), 255-63.
Nair CN and Davis R., "Photochemical inhibition of poliovirus replication by 4,5',8-trimethylpsoralen plus light", Intervirology, 1978; 9(2), 65-75.
Neu, Wenby and Meiselman, "Effects of dextran molecular weight on red blood cell aggregation", Biophys J. Sep. 15, 2008 95(6), 3059-65.
Omenyi, Snyder and van Oss, "Effects of DMSO on the Properties of Red Blood cells I. Interaction with Lanthanum Ions and Flocculation", Journal of Dispersion Science and Technology, 1985, (6)4 1985, 391-411.
Omenyi et al., "Effects of DMSO on the properties of red blood cells II. Electrokinetics and sedimentation"; Journal of Dispersion Science and Technology 1986, 7(1), 1-19.
Parichehreh et al., "Microfluidic inertia enhanced phase partitioning for enriching nucleated cell populations in blood", Lab Chip, 2013, 13, 892.
Richman, "Prolonged cryopreservation of human granulocytes", Transfusion, Nov.-Dec. 1983, 23(6), 508-11.
Rowley and Anderson, "Effect of DMSO exposure without cryopreservation on hematopoietic progenitor cells", Bone Marrow Transplant, May 1993, 11(5), 389-93.
Sala-Trepat JM, Savage MJ and Bonner J., "Isolation and characterisation of poly(adenylic acid)-containing messenger ribonucleic acid from rat liver polysomes", Biochim Biopys Acta, Jun. 22, 1978, 519(1), 173-93.
Sewchand LS and Canham PB, "Modes of rouleaux formation of human red blood cells in polyvinylpyrrolidone and dextran solutions", Can J Physiol Pharmacol, Nov. 1979, 57(11), 1213-22.
Sinsheimer RL, Starman B, Nagler C Guthrie S, "The process of infection with bacteriophage phi-XI74. I. Evidence for a replicative form" J Mol Biol. Mar. 1962; 4:142-60.
Solves et al., "Qualitative and quantitative cell recovery in umbilical cord blood processed by automated devices in routine cord blood banking: a comparative study", Blood Transfus., Jul. 2013; 11(3), 405-411.
Wagner, J. E., "Umbilical Cord Blood Stem Cell Transplantation" Am J Ped Hematol Oncol, 1993, 15, 169.
"CryoPur-D™: 55% w/v DMSO, Buffered with 5% w/v Dextran-40" Data Sheet, OriGen Biomedical Inc. product page, Mar. 6, 2014, extracted from the internet: http://wvvw.origen.com/products/Cryopreservation/CryoPur; 1 page.

* cited by examiner

METHODS OF CELL SEPARATION

This invention relates to methods and compositions for separating and/or priming cells, and more particularly to methods and compositions for separating erythrocytes from peripheral blood, bone marrow, umbilical cord blood and related blood tissues.

Isolation of white cells from blood for in vitro studies or in cellular therapy usually incorporates an initial separation of blood mainly based on the bulk depletion of erythrocytes, which comprise >99% of the cellular mass.

Techniques for erythrocyte removal are based on hypotonic lysis of erythrocytes, density gradient separation, enhanced centrifugal sedimentation using hydroxyethyl starch or mixtures (containing amongst other things antibodies) that promote accelerated sedimentation of the erythrocytes.

Hypotonic lysis, while useful in low volume in vitro studies, can be impractical for the large volumes of blood tissues processed for cellular therapies. In cell therapy procedures, erythrocyte hypotonic lysis is usually performed as a final step to remove the remaining contaminating erythrocytes in a sample after bulk depletions by other methods.

Density-gradient separation relies on differences in the densities of cell types that causes them to segregate at different levels in a fluid medium of variable density. Differences in density between the cell types can be small, and different cell types can be heterogeneous in size and density. Consequently, particular cell types can become distributed throughout a density-gradient medium rather than precisely segregating at a discrete area in the density medium, resulting in reduced recovery of desired cells and/or contamination with undesired cell types.

In procedures that enrich for rare blood cell types such as hematopoietic progenitor cells, density-gradient sedimentation can lead to loss or reduced yields of desired cell subsets. For example, using conventional density-gradient methods to isolate progenitor cells from umbilical cord blood results in a significant loss of the desired stem cells e.g., $CD34^+$ hematopoietic stem cells (HSCs) or VSELs (Very Small Embryonic Like Stem Cells) (Wagner, J. E., Am J Ped Hematol Oncol 15:169 (1993)). Using conventional density-gradient methods to isolate lymphocytes can result in selective loss of particular lymphocyte subsets. (Collins, J Immunol Methods 243:125(2000)).

These separation methods have an additional contraindication for use in cellular therapies in that the chemical entities in the separation medium can be toxic if infused with the cells into the recipient. As such, additional steps must be performed to ensure their complete removal prior to infusion. Instrument methodologies such as elutriation also depend upon differential separation of blood components by density and can suffer from similar deficiencies in performance.

Another method for removing erythrocytes from blood utilises hydroxyethyl starch which stimulates erythrocyte aggregation, which then sediment more rapidly than leukocyte components when sedimented at 50×g in a centrifuge. While this method is generally non-toxic for the recipient, its performance in the recovery of important cell types, including, for example, mesenchymal stem cells (MSCs) hematopoietic stem cells (HSCs) and VSELs is variable and with respect to umbilical cord blood, for example, can result in less-than-ideal recovery of stem cells and diminution of the engraftment potential of the cord blood cells, increasing the risk for transplant failure.

A more recently reported methodology has been disclosed (EP 2,117,592; U.S. Pat. No. 7,598,089) and involves the mixing of uncoaggulated blood with a composition comprising: dextran; anti-glycophorin A antibody; in addition to other antibody species (e.g. anti-CD9 antibodies; anti-CD15 antibody; and tandem antibodies, in which two different antibodies have been joined together to form a single entity). Antibodies represent an expensive solution to methods of cell separation and recovery of nucleated cells of interest from blood.

Increasing the recovery of rare cell types from donor tissue would dramatically improve the outcome of transplant and immune therapies (e.g., bone marrow transplants, stem cell-based gene therapy, and immune cell therapy), the success of which is related to the actual number of the cells being introduced for the therapeutic application. It is also desirable to provide a method of cell separation which results in high proportions of viable cells of interest.

SUMMARY OF THE INVENTION

The present invention relates to the finding that certain compounds, namely dimethyl sulphoxide (DMSO) and certain amino acids, have surprisingly advantageous effects when brought into contact with blood cells in combination with a macromolecular erythrocyte sedimentation enhancer—some of these effects become apparent only when the blood cells at issue are subsequently subjected to certain processing. In particular, the use of these compounds in combination with a macromolecular erythrocyte sedimentation enhancer enables the recovery of higher quantities of non-erythrocyte blood cells from a blood cell-containing sample. These compounds can also be used in combination with a macromolecular erythrocyte sedimentation enhancer to prime non-erythrocyte blood cells so as to protect their integrity in subsequent cryopreservation step(s), thus also enabling higher quantities of non-erythrocyte blood cells to be recovered following cryopreservation. Thus, the present inventor has developed a method of treating blood samples to achieve separation of red and white blood cells. The method also accelerates the separation of red and white blood cell fractions and does not rely on the use of antibodies. The present inventor has also developed a method of priming a cell fraction for cryopreservation.

DETAILED DESCRIPTION OF THE INVENTION

The present invention provides the use of a combination of:

(i) a macromolecular erythrocyte sedimentation enhancer, and (ii) dimethyl sulphoxide (DMSO), dimethylglycine (DMG) and/or valine;

to recover non-erythrocyte blood cells from a blood cell-containing sample and/or to prime non-erythrocyte blood cells to protect their integrity in subsequent cryopreservation step(s). Preferably, the macromolecular erythrocyte sedimentation enhancer is dextran and component (ii) is DMSO.

When the combination of components (i) and (ii) is used to recover non-erythrocyte blood cells from a blood cell-containing sample, component (ii) can be used to enable the recovery of more viable non-erythrocyte blood cells from the blood cell-containing sample than would be obtained using component (i) alone.

When components (i) and (ii) are used in accordance with the present invention, the components are typically used at relatively low concentrations, compared to e.g. the concentrations at which agents such as dextran and/or DMSO may be used when employed as cryoprotectants. When the non-erythrocyte blood cells are contacted with components (i) and (ii), the resulting mixture may comprise component (i) at a concentration of 0.01 to 20% w/v, preferably 0.05 to 10% w/v, e.g. 0.1 to 5% w/v (such as 0.5 to 2% w/v, 1 to 1.5% w/v, or at or around 1.25% w/v), or 2 to 10% w/v (such as 5 to 7.5% w/v, 6 to 6.5% w/v, or at or around 6.25% w/v). Preferably, when the non-erythrocyte blood cells are contacted with components (i) and (ii), the mixture comprises component (ii) at a concentration of 0.01 to 20% v/v, preferably 0.05 to 10% v/v, e.g. 0.1 to 5% v/v (such as 0.5 to 2% v/v, 1 to 1.5% v/v, or at or around 1.25% v/v), or 2 to 10% v/v (such as 5 to 7.5% v/v, 6 to 6.5% v/v, or at or around 6.25% v/v). Typically, the concentration of component (i) in % w/v is approximately the same as the concentration of component (i) in % v/v, although the concentration of component (ii) may at times be higher, e.g. up to two, three, four, or five times higher.

Preferably, when the combination of components (i) and (ii) is used to prime non-erythrocyte blood cells to protect their integrity in subsequent cryopreservation step(s), this priming step is distinct from any steps that would be taken in order to place the cells in a form ready for direct cryopreservation/freezing. In other words, before the primed non-erythrocyte blood cells are subjected to cryopreservation, a further step of adding an appropriate amount of cryoprotectant is appropriate. In this regard, for the formulation intended for cryopreservation it may be advantageous to use a cryoprotectant which comprises at least one of components (i) or (ii), which will be present already from the priming step. That way, there is no need to recover the cells from the priming composition—rather, one or more additional cryoprotectant agents can just be added to the mixture of the cells and the priming composition.

Preferably, when the combination of components (i) and (ii) is used to prime non-erythrocyte blood cells to protect their integrity in subsequent cryopreservation step(s), the subsequent cryproservations step(s) may refer to one or more of the steps of (b) adding a cryoprotectant to the thus obtained non-erythrocyte blood cells, (c) cryopreserving the non-erythrocyte blood cells, (d) thawing the non-erythrocyte blood cells, and/or (e) recovering the non-erythrocyte blood cells from the cryopreserved formulation. Typically it refers to the step (b), to step (c), or to both of steps (b) and (c), as these are steps where the combination of components (i) and (ii) is particularly effective in helping protect cell integrity against the type of damage that may otherwise occur in the absence of the combination of components (i) and (ii) (i.e. even if just one of these components was present in the absence of the other).

As will be appreciated, components (i) and (ii) can of course be used to prime non-erythrocyte blood cells in the form of a cell fraction that has already undergone a treatment(s) to remove erythrocytes and/or one or more specific nucleated cells so as to attain a specific desired subset of white blood cells. However, since the cell separation method of the present also serves to protect the resulting (separated/recovered) cells against damage by subsequent cryopreservation step(s)), simply using the cell separation method of the present invention can be much more efficient, as benefits similar to those which arise in the priming method of the invention can be enjoyed without the need for two separate (separation and priming) treatment steps.

Thus, the present invention provides a method for separating cells, said method comprising:

(a) contacting a blood cell-containing sample with:
(i) a macromolecular erythrocyte sedimentation enhancer, and
(ii) DMSO, DMG and/or valine;
(b) allowing said sample to partition into a sedimented phase and a supernatant phase; and
(c) recovering cells from said sedimented and/or supernatant phase.

The combination of components (i) and (ii) enables the recovery of more viable non-erythrocyte blood cells than could be obtained using component (i) alone. This advantage arises both (a) following the separation step, and (b) following subsequent cryopreservation step(s).

Preferably, step (a) comprises contacting a blood cell-containing sample with a composition comprising the components (i) and (ii). As mentioned below, a preferred agent for use as component (i) is dextran.

Preferably, component (ii) is DMSO, DMG or valine.

Preferably, step (c) comprises recovering cells from said sedimented or said supernatant phase.

Thus, in a preferred aspect, the present invention provides a method for separating cells, said method comprising:
a) contacting a blood cell-containing sample with a composition comprising:
I) dextran; and
II) dimethyl sulphoxide (DMSO), dimethylglycine (DMG) or valine
b) allowing said sample to partition into a sedimented phase and a supernatant phase; and
c) recovering cells from said sedimented phase or said supernatant phase.

Preferably, in the method of the invention for separating cells, step (a) comprises contacting a blood cell-containing sample with a composition comprising components (i) and (ii), wherein the blood cell containing sample and the composition are mixed at a ratio of 10:1 to 1:10 by volume (ratios of components mentioned herein are generally intended to refer to ratios by volume unless indicated otherwise), preferably 5:1 to 1:5, more preferably 2:1 to 1:2. Typically, the ratio is at or about a ratio of 1:1.

The exact ratio used may depend on the concentration of components (i) and (ii) in the composition. Thus, one particularly preferred composition for use in the present invention is a composition that is based on PBS, and which is prepared by combining equal amounts (by volume) of 5% w/v Dextran 500 in PBS, and 5% v/v DMSO in PBS (unless indicated otherwise, concentrations of component (i) mentioned herein are generally intended to refer to units of % w/v, and concentrations of component (ii) mentioned herein are generally intended to refer to units of % v/v). This composition is referred to herein as "TotiCyte 1×", and contains 2.5% w/v Dextran 500 and 2.5% v/v DMSO in PBS. The above-mentioned ratios are particularly preferred when this composition is being used. However, the concentration of components (i) and (ii) in the composition can be varied. For instance, an alternative composition for use according to the invention is a more concentrated formulation referred to herein as "TotiCyte 5×" refers to a TotiCyte composition based on PBS and containing 7.5% w/v Dextran 500 and 7.5% v/v DMSO. When compositions such as this one are being used, the preferred ratios may be adjusted so as to decrease the proportion of the composition, e.g. to a third, a quarter, or fifth. Thus, in this embodiment it may be more preferred for the blood cell containing sample and the composition to be mixed at a ratio of 50:1 to 1:2 by volume, preferably 25:1 to 1:1, more preferably 10:1 to 5:2. Typically, the ratio is at or about a ratio of 5:1.

Thus, generally in the context of the present invention, it is preferred for the blood cell containing sample and the composition to be mixed at a ratio of 50:1 to 1:10 by volume, preferably 25:1 to 1:5, more preferably 10:1 to 1:2.

The ratio at which to mix the blood cell containing sample with components (i) and (ii) may also be defined with reference to the concentration of components (i) and (ii) in the resulting mixture. Preferably the blood cell-containing sample and component (i) are combined so as to provide a concentration of component (i) in the resulting mixture of 0.1 to 8% w/v, preferably 0.25 to 5% w/v, more preferably 0.5 to 2% w/v, yet more preferably 1 to 1.5% w/v, and typically at or around 1.25% w/v. Preferably the blood cell-containing sample and component (ii) are combined so as to provide a concentration of component (ii) in the resulting mixture of 0.1 to 8% v/v, preferably 0.25 to 5% v/v, more preferably 0.5 to 2% v/v, yet more preferably 1 to 1.5% v/v, and typically at or around 1.25% v/v. Typically the concentrations for components (i) and (ii) are approximately the same. Thus, in one preferred aspect of the separation method of the invention, once the blood cell-containing sample has been contacted with components (i) and (ii), the concentration of component (i) is 0.25 to 5% w/v, and the concentration of component (ii) is 0.25 to 5% v/v.

Target concentrations in the (cell +composition) mixtures can be higher if a more concentrated composition of components (i) and (ii) is being used, such as TotiCyte 5×. Thus, more generally the target concentration for component (i) is 0.1 to 10% w/v, preferably 0.5 to 5% w/v, more preferably 1 to 4% w/v, and typically at or around 1.25 or 2% w/v; and the target concentration for component (ii) is 0.1 to 10% v/v, preferably 0.5 to 5% v/v, more preferably 1 to 4% v/v, and typically at or around 1.25 or 2% v/v.

In the cell separation method of the invention, when step (a) comprises contacting a blood cell-containing sample with a composition comprising components (i) and (ii), this composition preferably comprises 0.5-10% (more preferably 1-5%, typically 2-4%) w/v of component (i) and 0.5-10% (more preferably 1-5%, typically 2-4%) v/v of component (ii).

Preferably, the blood cell-containing sample on which the method of the invention is carried out is selected from peripheral blood, umbilical cord blood and bone marrow.

Preferably, the blood cell-containing sample on which the method of the invention is carried out is taken from a human. It is also preferred for the blood cell-containing sample to contain an anticoagulant. The nature of the anticoagulant is not particularly limited—typical examples include heparin, EDTA, CPD and CPDA, with CPD and CPDA being preferred, and CPDA most preferred.

Preferably, the separation method of the present invention is for recovering non-erythrocyte blood cells from a blood cell-containing sample containing erythrocyte blood cells. Thus, typically the removes substantially all of the erythrocytes, e.g, at least 90%, preferably at least 95%, more preferably at least 98% and typically at least 99% of the erythrocytes present in the starting blood cell-containing sample.

Preferably, the separation method of the present invention is for use in preparing a sample of non-erythrocyte blood cells having a haematocrit of less than 1% (by volume). Thus, the cells that are recovered from said sedimented and/or supernatant phase in step (c) preferably have a haematocrit of no more than 1%, and more preferably less than 1%.

In one embodiment, the separation method of the present invention is for preparing a sample of concentrated platelets.

The methods of the present invention enable the recovery of enhanced proportions of non-erythrocyte blood cells, typically white blood cells. In the context of the separation method of the invention, the level of recovery for the or each of the desired non-erythrocyte blood cell type(s) is preferably at least 80%, preferably at least 90%, and more preferably at least 95% relative to the amount in the starting whole blood sample. The post thaw recovery levels obtainable by using the separation or priming methods of the invention preferably enable recovery levels of at least 60%, more preferably at least 80%, and typically at least 90% (particularly if the recovery levels are measured before any washing steps that may be carried out post thaw). Suitable methods for measuring the concentration of such desired cell types, such as the total nucleated cell (TNC), CD34 and CD45 cell counts are discussed below in the Examples.

In the separation method of the invention, in step (b) the sample is preferably allowed to partition into a sedimented phase and a supernatant phase for 10 to 60 minutes.

The present invention also provides a method for priming a non-erythrocyte blood cell fraction for crypreservation, said method comprising contacting the cell fraction with a combination of:
  (i) a macromolecular erythrocyte sedimentation enhancer, and
  (ii) DMSO, DMG and/or valine;
wherein when the blood cell-containing sample is contacted with components (i) and (ii), the concentration of component (ii) does not exceed 5% v/v. Preferably in this regard, the concentration of component (ii) does not exceed 4% v/v, more preferably it does not exceed 3% v/v, more preferably still it does not exceed 2% v/v, and typically it does not exceed 1.5% v/v.

Preferred aspects described above for the use of the components (i) and (ii) in the separation method of the invention are also preferred for the priming method of the invention.

For instance, the priming method of the invention preferably comprises contacting the cell fraction with a composition comprising components (i) and (ii), wherein the cell fraction and the composition are mixed at a ratio of 10:1 to 1:10 by volume, preferably 5:1 to 1:5, more preferably 2:1 to 1:2. Typically, the ratio is at or about a ratio of 1:1.

As above, though, the exact ratio used may depend on the concentration of components (i) and (ii) in the composition. Thus, the above-mentioned ratios are particularly preferred when the "TotiCyte 1×" composition of the invention is being used.

However, the concentration of components (i) and (ii) in the composition can be varied. For instance, when the "TotiCyte 5×" composition of the invention is being used, the preferred ratios may be adjusted so as to decrease the proportion of the composition, e.g. to a third, a quarter, or a fifth. Thus, in this embodiment it is more preferred for the cell fraction and the composition to be mixed at a ratio of 50:1 to 1:2 by volume, preferably 25:1 to 1:1, more preferably 10:1 to 5:2. Typically, the ratio is at or about a ratio of 5:1.

Thus, generally in the context of the present invention, it is preferred for the cell fraction and the composition to be mixed at a ratio of 50:1 to 1:10 by volume, preferably 25:1 to 1:5, more preferably 10:1 to 1:2.

The ratio at which to mix the cell fraction with components (i) and (ii) may also be defined with reference to the concentration of components (i) and (ii) in the resulting mixture. Preferably the cell fraction and component (i) are combined so as to provide a concentration of component (i)

in the resulting mixture of 0.1 to 8% w/v, preferably 0.25 to 5% w/v, more preferably 0.5 to 2% w/v, yet more preferably 1 to 1.5% w/v, and typically at or around 1.25% w/v. Preferably the cell fraction and component (ii) are combined so as to provide a concentration of component (ii) in the resulting mixture of 0.1 to 8% v/v, preferably 0.25 to 5% v/v, more preferably 0.5 to 2% v/v, yet more preferably 1 to 1.5% v/v, and typically at or around 1.25% v/v. Typically the concentrations for components (i) and (ii) are approximately the same. Thus, in one preferred aspect of the priming method of the invention, once the cell fraction has been contacted with components (i) and (ii), the concentration of component (i) is 0.25 to 5% w/v, and the concentration of component (ii) is 0.25 to 5% v/v.

Target concentrations in the (cell +composition) mixtures can be higher if a more concentrated composition of components (i) and (ii) is being used, such as TotiCyte 5×. Thus, more generally the target concentration for component (i) is 0.1 to 10% w/v, preferably 0.5 to 5% w/v, more preferably 1 to 4% w/v, and typically at or around 1.25 or 2% w/v; and the target concentration for component (ii) is 0.1 to 10% v/v, preferably 0.5 to 5% v/v, more preferably 1 to 4% v/v, typically at or around 1.25 or 2% v/v, and most typically at or around 1.25% v/v.

The priming method of the invention preferably comprises contacting the cell fraction with a composition comprising components (i) and (ii), wherein the composition comprises 0.1-10% (more preferably 0.5-5%, typically 1-2%) w/v of component (i) and 0.1-10% (more preferably 0.5-5%, typically 1-2%) v/v of component (ii).

Preferably, the cell fraction comprises white blood cells.

Preferably, the cell fraction is taken from a human.

In a preferred aspect, the separation and priming methods of the present invention are for (the purpose of) increasing the proportion of viable white blood cells recovered following subsequent cryopreservation step(s). In particular, introducing component (ii) enhances the quantity of viable cells that can be recovered following cryopreservation, as compared to what is possible with component (i) alone. As noted above, this reference to cryopreservation step(s) may refer to one or more of the steps of (b) adding a cryoprotectant to the thus obtained non-erythrocyte blood cells, (c) cryopreserving the non-erythrocyte blood cells, (d) thawing the non-erythrocyte blood cells, and/or (e) recovering the non-erythrocyte blood cells from the cryopreserved formulation, but typically it refers to step (b), to step (c), or to both of steps (b) and (c).

As regards component (i) for use in accordance with the methods and compositions of the present invention, there is no specific limitation as to the type of macromolecular erythrocyte sedimentation enhancer that can be used. Possible substances that may be used include polybrene, protamine sulphate, polyethylene glycol (PEG), hydroxyethyl starch (HES), polyvinyl pyrrolidone (PVP), and dextrans (preferably dextrans with a molecular weight of at least around 50 kDa). Preferably component (i) is a polysaccharide, and more preferably it is dextran. As regards its size, component (i) (which preferably is dextran) preferably has a molecular weight of at least 50 kDa, more preferably at least 70 kDa, yet more preferably at least 100 kDa or at least 200, 300 or even 500 kDa. There is no specific upper limit for the molecular weight, although typically it 1000 kDa or less, more typically 750 kDa or less, yet more typically 500 kDa or less. A particularly preferred dextran is dextran 500. A molecular weight within these preferred ranges (at least 50 kDa, etc) is particularly preferred in the context of the priming method of the invention.

As regards component (ii) for use in accordance with the methods and compositions of the present invention, this may be a mixture of two or all of DMSO, DMG and valine, but typically just one of these agents is used. The agent valine is preferably L-valine. Generally, DMSO and valine (typically L-valine) are more preferred, with DMSO being most preferred.

Preferably, component (i) is dextran and component (ii) is DMSO. More preferably, component (i) is dextran 500 and component (ii) is DMSO.

Component (i) is preferably brought into contact with the sample or cell fraction in the form of a composition, typically an aqueous solution. Preferably the composition is a saline solution. Preferably the pH of the solution is 6.8 to 7.8, e.g. at or around 7.4. Typically the solution is buffered to the desired pH using a pharmaceutically acceptable buffer. Possible solvents for use in this regard include PBS (phosphate buffered saline), MOPS and HEPES, with PBS being preferred.

Component (ii) is preferably brought into contact with the sample or cell fraction in the form of a composition, typically an aqueous solution. Preferably the composition is a saline solution. Preferably the pH of the solution is 6.8 to 7.8, e.g. at or around 7.4. Typically the solution is buffered the desired pH. Possible solvents for use in this regard include PBS (phosphate buffered saline), MOPS and HEPES, with PBS being preferred.

Preferably, components (i) and (ii) are combined into a single composition before being brought into contact with the blood cell-containing sample or cell fraction. This single composition typically consists essentially of the solvent (preferably PBS) and each of components (i) and (ii).

The present invention also provides a method for preparing non-erythrocyte blood cells for cryopreservation, which method comprises (a) a separation or priming method of the invention as defined herein, and (b) adding a cryoprotectant to the thus obtained non-erythrocyte blood cells.

The present invention also provides a method for the cryopreservation of non-erythrocyte blood cells, which method comprises (a) a separation or priming method of the invention as defined herein, (b) adding a cryoprotectant to the thus obtained non-erythrocyte blood cells, and (c) cryopreserving the non-erythrocyte blood cells.

The present invention also provides a method for the cryopreservation and subsequent recovery of non-erythrocyte blood cells, which method comprises (a) a separation or priming method of the invention as defined herein, (b) adding a cryoprotectant to the thus obtained non-erythrocyte blood cells, (c) cryopreserving the non-erythrocyte blood cells, and (d) thawing the non-erythrocyte blood cells. There may also be a further step (e) of recovering the non-erythrocyte blood cells from the (by now thawed) cryopreserved formulation.

Preferred formulations for the cryoprotectant are discussed above. Preferably the cryoprotectant comprises DMSO. In one embodiment it may consist essentially of DMSO.

Cryopreservation typically involves reducing the temperature to sub-zero temperatures, i.e. less than 0° C. Typically it may involve the reduction of the temperature to −50° C. or less, such as to around −80° C. (e.g. −78° C.), but it may involve the reduction of the temperature to −100° C. or less, such as to around −120° C. or less, or even −140° C. or less.

The present invention also provides a fraction of non-erythrocyte cells obtainable by a method of the invention as defined herein. Typically such cell fractions may be distinguished from cell fractions obtained using other methods by the characteristic high proportions of viable non-erythrocyte blood cells. They may also be distinguished from cell fractions obtained via other methods by virtue of the protective effect that will arise during subsequent cryopreservation step(s). There may also be a small remaining level of component (i) and/or (ii) in a cell fraction that has been prepared via a method of the present invention.

The present invention also provides a composition comprising (i) a macromolecular erythrocyte sedimentation enhancer, and (ii) DMSO, DMG and/or valine, which composition is suitable for use in recovering non-erythrocyte blood cells from a blood cell-containing sample and/or priming non-erythrocyte blood cells to protect their integrity in subsequent cryopreservation and thawing steps, wherein if component (ii) is DMSO, then the concentration of DMSO in the composition is 10% v/v or less. Preferably in this regard, the concentration of component (ii) does not exceed 8% v/v, more preferably it does not exceed 6% v/v, yet more preferably it does not exceed 4% v/v, and typically it does not exceed 3% v/v.

The concentration of component (i) in the composition may advantageously be 10% w/v or less, preferably 8% w/v or less, more preferably 6% w/v or less, yet more preferably 4% w/v or less, typically 3% w/v or less. The concentration of component (i) in the composition is preferably 0.1% w/v or more, more preferably 0.5% w/v or more, more preferably still 1% w/v or more, typically 2% w/v or more.

The concentration of component (ii) in the composition is preferably 8% v/v or less, more preferably 6% v/v or less, more preferably still 4% v/v or less, typically 3% v/v or less. The concentration of component (i) in the composition is preferably 0.1% v/v or more, more preferably 0.5% v/v or more, more preferably still 1% v/v or more, typically 2% v/v or more.

In one preferred aspect of the composition, the concentration of component (i) is 1-5% w/v and the concentration of component (ii) is 1-5% v/v.

The present invention also provides an apparatus comprising a composition (comprising components (i) and (ii)) as defined herein, which apparatus is a bottle, a blood bag, a pre-filled syringe for injection into a blood bag, or a kit comprising the composition, and a blood collection vessel.

The component (i) (e.g. dextran) and component (ii) (the dimethyl containing component) together provide a surprisingly and synergistically effective separation and/or priming medium which allows for (i) the enhanced partitioning into red and white cell fractions (and plasma fraction) of a sample comprising blood cells, (ii) improved levels of cell recovery following separation, and/or (iii) a protective effect to be imparted to non-erythrocyte blood cells which protects their integrity in subsequent cryopreservation step(s). The separation medium facilitates gravity assisted sedimentation and therefore step (b) generally requires nothing more than leaving the combination of sample and separation medium to stand. Thus, typically no active steps are needed in step (b), and it is possible simply to rely on gravity to help bring about the desired sedimentation. For the avoidance of doubt, though, step (b) does not exclude the possibility of active steps being taken, provided that any such steps do not prevent the partitioning.

Step a) in the method of the invention for separating cells will typically comprise a mixing step. A separation medium (i.e. a composition comprising components (i) and (ii)) and blood cell-containing sample are conveniently mixed at a ratio of 2:1 to 1:2, preferably at or about a ratio of 1:1.

In a further aspect, the invention provides a composition suitable for use as a blood cell separation medium comprising component (i) (e.g. dextran) and dimethylsulphoxide, dimethylglycine or valine. The use of such a composition in a blood cell separation method constitutes a further aspect of the present invention. In one aspect of the invention, the composition typically comprises 3-15, preferably 4-10% w/v dextran and 1-10, preferably 3-8% v/v dimethylsulphoxide, dimethylglycine or valine.

The invention provides efficient and cost effective methods and compositions for separating and recovering therapeutically or diagnostically valuable cells from peripheral blood, umbilical cord blood, and bone marrow (e.g. a bone marrow aspirate); umbilical cord blood is especially preferred for treatment in accordance with the methods of the invention. In particular, the invention provides methods and compositions for specifically removing the erythrocyte component of the blood.

The disclosed compositions and methods can be used, for example, to prepare cells for tissue culture, immunophenotypic characterization, other diagnostic testing, further purification and therapeutic administration. In particular, the methods can be used to prepare cells for long term storage, e.g. cryopreservation. There is demand for storage of cord blood when a child is born for the therapeutic potential of cells within cord blood to address conditions later in life. For example, HSCs could be used to treat leukaemia and lymphoma; MSCs could treat heart disease, Alzheimer's Disease or Parkinson's Disease and be used to regenerate bone, cartilage, muscle or connective tissue; VSELs could regenerate neural, cardiac or muscle cells.

The therapeutic potential of pluripotent cells is increasing all the time and the benefits of an autologous supply clear. However, there is a cost associated with long term storage which means that enrichment for cells of interest (i.e. exclusion of erythrocytes to reduce the sample size) is desirable. However, it is important that the small numbers of key cells, such as VSELs, are not further diminished by such separation. The present invention addresses these needs.

Cells can be recovered from either or both the sedimented phase (aggregate) or supernatant phase. According to the methods of the invention, even very rare cell types can be recovered in relatively high yield. The sedimented phase contains the majority of erythrocytes from the sample while the supernatant contains the nucleated cells. The nucleated cells are also referred to as the "white blood cells" and include the lymphocytes and stem cells. The "non-erythrocyte" cells mentioned herein may preferably refer to one or more of these cells.

The disclosed compositions and methods can be used to isolate and enrich for a variety of cell types, including, for example, T lymphocytes, T helper cells, T suppressor cells, T killer cells, B cells, NK cells, hematopoietic stem cells, non-hematopoietic stem cells, VSELs or other cells in the blood circulatory system. The "non-erythrocyte" cells mentioned herein may preferably refer to one or more of these cells.

The disclosed methods can be applied to cells of any mammalian blood system including humans, non-human primates, rodents, swine, bovines, dogs, cats and equines. Samples containing human blood cells are especially preferred. The blood cell-containing sample may be whole blood or tissue or partially purified, e.g. to form a crude reduction in the erythrocyte content. For the avoidance of doubt, the methods of the present invention are for use in connection with in vitro processing of blood cell-containing samples, non-erythrocyte cells and cell fractions, i.e. the cells have been removed from the human (or animal) prior to carrying out the methods of the invention.

According to the separation method of the invention, step (b), the partition step, preferably lasts for at least 10 minutes, more preferably at least 15 minutes, and can continue for e.g. up to 1 or 2 (or more) hours, but typically no more than 1 hour is needed. Thus, the partition step is typically 10 to 60 minutes, preferably 15-35 minutes. Preferably adequate partition is achieved within 30 minutes. 'Adequate partition' can be measured as at least 90 or 95% of the maximum partition the system can achieve if left for 12 hours.

According to the priming methods of the invention, the priming treatment typically involves contacting the cell fraction with components (i) and (ii) for at least 10 minutes, preferably at least 20 minutes. Priming can continue for e.g. up to 1 or 2 (or more) hours, but typically no more than 1 hour is needed, e.g. around 30 to 50 minutes is preferred.

Dextran is a polysaccharide consisting of glucose units linked predominantly in alpha (1 to 6) form. Dextran can cause stacking of erythrocytes (i.e., rouleau formation) and thereby facilitate the removal of erythroid cells from solution. Typically, the concentration of component (i) (e.g. dextran) in the cell separation composition is 10 to 40 g/L (e.g., around 20 g/L). Occasionally the concentration of component (i) (e.g. dextran) used is higher than 20 g/L (e.g. 25g/L or even higher). Cell aggregation by rouleau can take an extended period of time such that use of component (i) (e.g. dextran) alone is not a commercially viable separation technique.

In one aspect of the invention, the final concentration of component (i) (e.g. dextran) when mixed with the sample or cell fraction is typically 1-20%, preferably 1.5 to 10%, more preferably 2.5-10% w/v.

References to dextran include dextran salts, e.g. dextran sulphate sodium salt. Dextran products vary significantly in their molecular weight; preferably, the dextran used in the present invention has a molecular weight of greater than 50, more preferably 50-1,000 kilodaltons, especially preferred are molecular weights of 200-750, e.g. about 500 kilodaltons.

When DMSO, DMG or valine is combined with component (i) (e.g. dextran) and contacted with the blood cell containing sample, a greater proportion of white blood cells can be recovered than if component (i) is used alone. Also, the thus obtained cells acquire some form of protection which helps preserve their integrity if the cells are subsequently subjected to cryopreservation. Further, sedimentation of a population of erythrocytes, e.g. using TotiCyte 1×, may occur much more quickly than with dextran alone, preferably within 15-30 minutes.

In one embodiment, DMSO, DMG or valine is typically present at a final concentration (when mixed with the sample) of 0.25 to 10% w/v, preferably 0.5-5% w/v, more preferably 2-3%, e.g. about 2.5%.

In one embodiment, the ratio of component (i) (e.g. dextran) to component (ii) (the dimethyl compound) is typically 1:1 to 1:5, more typically 1:1 to 1:2, with a ratio of about 1:1 being preferred.

The cell separation composition of the invention typically comprises in an appropriate buffer (e.g. Phosphate buffered saline) and may contain divalent cations (e.g., $Ca^{+2}$ and $Mg^{+2}$). Divalent cations can be provided, for example, by a balanced salt solution (e.g., Hank's balanced salt solution), these are co-factors for selectin-mediated and integrin-mediated cell-to-cell adherence.

One of the advantages of the present invention over some of the prior art methods is that it enables the separation/removal of erythrocytes from a blood cell-containing sample with excellent recovery levels for the desired white blood cell fraction, without the need for antibodies. Thus, in one preferred aspect, the separation method of the present invention do not include the use of any antibodies, e.g. the composition(s) comprising components (i) and (ii) do not contain any antibodies. This may (optionally) be true also for the compositions used in the priming method of the invention. Notwithstanding this, as a practical matter it can be possible to introduce an antibody without prejudicing the benefits of the invention. Thus, the separation composition or medium of the invention may, but typically will not, additionally contain an appropriate antibody, antibody fragment, a tandem antibody or another molecule capable of specifically recognising a protein sequence or conformation. The separation compositions can include antibodies or fragments thereof to appropriate cell surface antigens, e.g. in order to encourage their co-sedimentation with the erythrocytes. The included antibodies or antibody fragments can be conjugated to a variety of functional groups known in the art (e.g. Streptavidin) which can be utilised to encourage sedimentation of a target population of cells upon introduction of a binding partner (e.g. Biotin).

After a sedimentation step, unsedimented cells can be recovered from the solution phase (i.e., the supernatant) by a variety of means, such as centrifugation of the resulting supernatant fraction. Cells also can be recovered from the sedimented phase. Sedimented cells can be dissociated by, for example, transferring the cells into buffers that contain divalent cation chelators such as EDTA or EGTA.

Cells recovered from the sedimented or unsedimented fraction can be further separated, isolated or purified, e.g. by using antibodies against cell surface antigens.

The separation method of the invention can be used to separate cells from a variety of blood-cell containing samples, including peripheral blood (e.g., obtained by venipuncture), umbilical cord blood (e.g., obtained postgravida), and bone marrow (e.g., from aspirate).

Umbilical cord blood is preferably subjected to the method of the invention within a week from birth, typically within 48, preferably within 24, more preferably within 12 hours. In a standard procedure, the umbilical cord is cleaned and blood bag needle inserted into the umbilical vein and arteries so that the blood passes into the bag which is then clamped and sealed. A courier service may be used to transport the sample to the site of performance of the cell separation method or it may be performed on the site of delivery of the infant.

The cell populations which are generated by the cell separation method of the invention can be used in the context of allogeneic and autologous transplantation. In the context of allogeneic transplantation, T lymphocytes can be removed from the cell transplant to reduce T lymphocyte-associated GvHD. In the context of autologous transplantation, undesired cells such as metastatic cancer cells from a patient's blood or bone marrow can first be removed before transplantation. Desirable cells (e.g., hematopoietic stem cells) then can be returned to the patient without, or substantially free of tumour cells.

The cell populations recovered according to the method of the invention, in particular the nucleated cells, preferably contain a good proportion of viable cells. The Examples describe, inter alfa, a method of assessing cell viability and, as an alternative, the Guava Personal Cell Analyser (PCA) Base System may be used to measure viability of a cell population of interest. The proportion of viable cells as measured using these techniques is preferably greater than 50%, more preferably greater than 55 or 60%.

The separation method of the present invention typically serves, primarily, to exclude erythrocytes and retain nucleated cells within a fraction of the starting sample and, as such, can be seen as a method of partial cell purification. However, the resulting fraction is likely to contain MSCs, HSCs and VESLs and so subsequent processing steps or modifications to the basic method described herein may be required to isolate a target population of interest. If a sample is cryopreserved, such subsequent steps may be performed when the sample is retrieved from a cryopreserved state.

The components of a composition for use according to the invention, i.e. a composition comprising components (i) and (ii) (also referred to herein as a cell separation composition) can be packaged individually or in admixture with one another. In a further aspect the present invention provides a kit comprising a cell separation composition of the invention (which may be in admixture or in separate containers) and a blood collection vessel (e.g., blood bag or vacuum tube). In some embodiments, the cell separation composition can be housed within a sterile bag. Furthermore, the sterile bag can be operably connected (e.g., via sterile tubing) to a processing bag, and the processing bag can be operably connected (e.g., via sterile tubing) to a storage bag or storage vessel to facilitate processing and sterile transfer of isolated cells. A single sterile bag can also perform the role of the processing bag. The storage bag or vessel can include additional cryopreservative such as dimethylsulphoxide sufficient to provide a final concentration of cryopreservative (DMSO) typically 1 to 10% of the final volume of solution. Cryopreservation can allow for long-term storage of these cells for therapeutic or research use. The packaging material included in a kit typically contains instructions or a label describing how the cell separation composition can be used to encourage the partitioning of particular types of cells. The kit may also contain a needle for collection of blood, the needle being integral with or connected to the blood collection vessel.

In other embodiments, a single bag may be used for cell separation and cryopreservation, with e.g. DMSO providing both separation and cryopreservation functions (DMSO may be present at a final concentration of around 2%). After the separation step within the bag, erythrocytes may be expelled using a valve or tube at the bottom of the bag before cryopreservation. The bag may be designed so that it can be hung during the separation step with the opening of the bag facing down so that only one opening is necessary for the filling of the bag and the removal of the erythrocytes.

Preferred features of the separation composition/medium discussed therein in the Examples and generally in relation to the methods are preferred features of the composition/medium per se and of the kit comprising the composition/medium.

The invention is further described in the following non-limiting Examples and with reference to the figures in which:

FIG. 1 shows clear separation of the erythrocytes (bottom of test tube) from the nucleated cells (top of test tube) in blood samples that were exposed to dextran 500 at a final concentration of 2.5% w/v and DMSO at a final concentration of either 2% v/v (left image) or 2.5% v/v (right image) for 30 minutes at room temperature.

FIG. 2 shows clear separation of the erythrocytes from the nucleated cells in blood samples that were exposed to dextran 500 at a final concentration of 2.5% w/v and DMSO at a final concentration varying from 1% v/v to 5% v/v. From left to right, the following final concentrations of DMSO were analysed (% v/v): 1, 1.5, 2, 2.5, 3, 3.5, 4, 4.5 and 5. The samples were exposed to the above solutions for either 15 minutes at room temperature (FIG. 2a) or for 30 minutes at room temperature (FIG. 2b).

FIG. 3 shows the erythrocyte volume fraction (haematocrit) of the nucleated cell fraction after cell separation. Blood samples were mixed at a ratio of 1:1 with either (i) PBS only (control, left), (ii) a solution containing 500 Mw dextran at a concentration of 5% w/v in PBS (final concentration of dextran of 2.5% w/v) (middle) or (iii) a solution containing 500 Mw dextran at a concentration of 5% w/v and DMSO at a concentration of 5% v/v in PBS (final concentration of dextran of 2.5% w/v and of DMSO of 2.5% v/v) (right). Samples were left to separate for 30 minutes at room temperature. Nucleated cell fractions (100 µl) were then transferred to a micropipette and centrifuged for 2 minutes at 1500 rpm.

FIG. 4 shows a dot plot of 7-Aminoactinomycin D (7-AAD) fluorescence levels (x-axis) against side scatter (y-axis). A blood sample was mixed at a ratio of 1:1 with a solution containing 500 Mw dextran at a concentration of 5% w/v and DMSO at a concentration of 5% v/v in PBS (final concentration of dextran of 2.5% w/v and of DMSO of 2.5% v/v). Samples were then left to separate for 30 minutes at room temperature before analysis was carried out using a "Stem Cell Enumeration Kit" obtained from Becton, Dickinson and Company.

FIG. 5 shows the separation of whole blood using constant 2.5% w/v Dextran 70 and other substances. Row 1=β-alanine; row 2=L-proline; row 3=L-valine; row 4=DMSO; and row 5=DMG. The left hand column shows each of the separations at 15 minutes, with the right column showing it after 30 minutes.

FIG. 6 shows a comparison of the separations of different Dextrans at a constant concentration of DMSO, after 30 minutes (see Example 5). Top left=Dextran 6 with control; Top right=Dextran 40; Bottom left=Dextran 70; Bottom right=Dextran 500.

Figure 9:
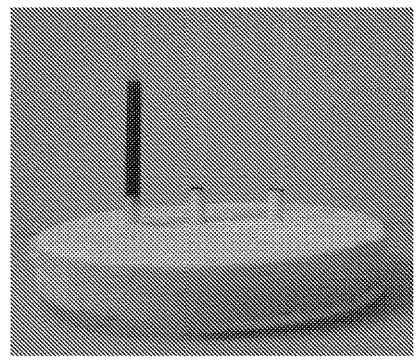

FIG. 9 shows haematocrit levels after whole blood separation and centrifugation. Prior to transferral to micropipettes, each mixture was left for 30 minutes to separate: the control had blood mixed 1:1 with PBS (left), the next tube had half Dextran half PBS mixed with blood (middle), the other had TotiCyte (right). Each were then transferred to micropipettes and centrifuged.

Figure 10:
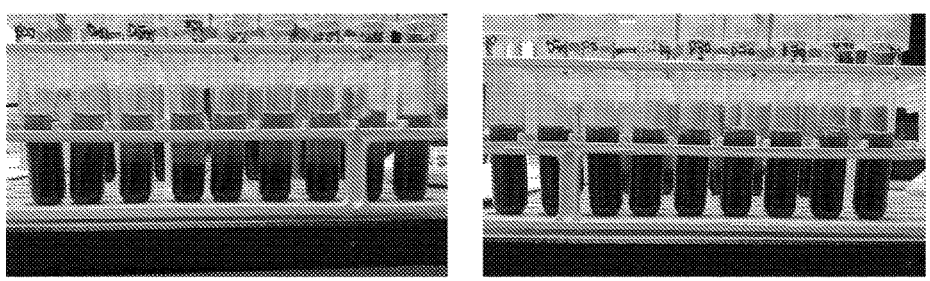
Figure 11:
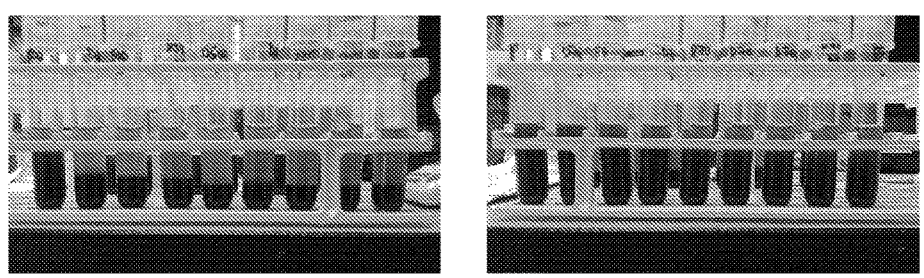
Figure 12:
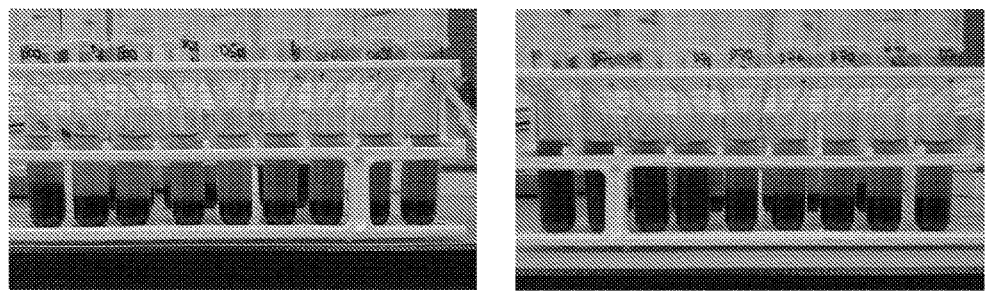

FIG. 10 shows (on the left) separation after 5 minutes using Dextran 500 at concentrations of 1, 1.5, 2, 2.5, 3, 3.5, 4, 4.5, and 5% w/v (left to right) mixed with 2.5% v/v DMSO. On the right is the same but with Dextran 70. FIGS. 11 and 12 show separation after 15 and 30 minutes, respectively.

Figure 13:
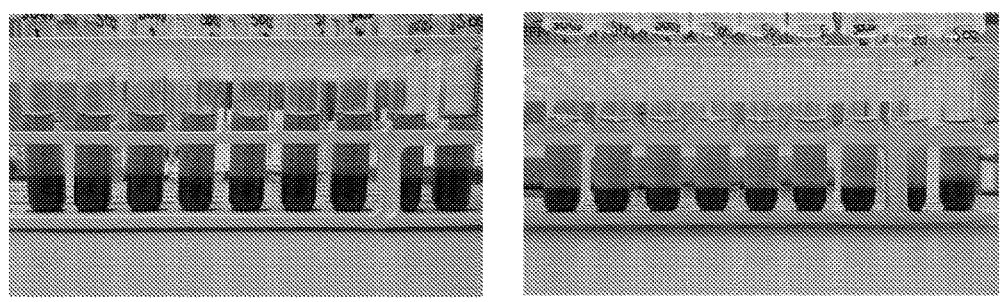

FIG. 13 shows separation using a 1:1 by volume combination of Dextran 500 at 2.5% w/v and DMSO at concentrations 1, 1.5, 2, 2.5, 3, 3.5, 4, 4.5, and 5% v/v. The left hand picture shows the separation after 15 minutes, at which point the separation is good. The right hand picture shows it after 30 minutes, where all concentrations work well and all have produced clear white cell fractions.

Figure 14:
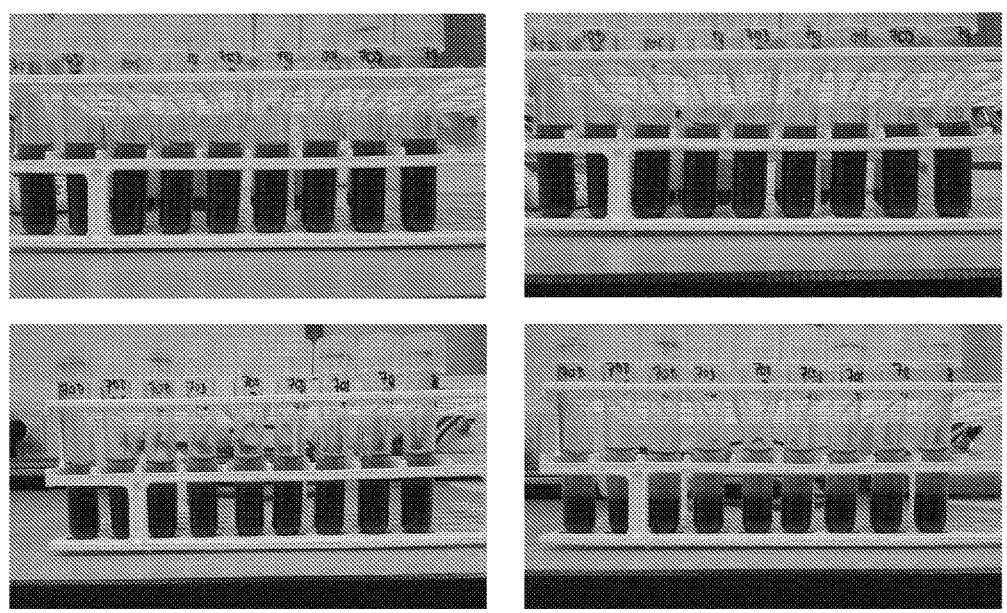

FIG. 14 shows separation using a 1:1 by volume combination of Dextran 70 at 1.5% w/v and DMSO at concentrations 1, 1.5, 2, 2.5, 3, 3.5, 4, 4.5, and 5% v/v. The top two images show the Dextran at a constant 1.5%, on the left at 15 minutes and on the right at 30 minutes. As can be clearly seen, it did not really separate the blood faster than the blood will separate out on its own. The bottom two images are of corresponding samples where a 3% w/v solution of Dextran 70 was used.

Figure 15:
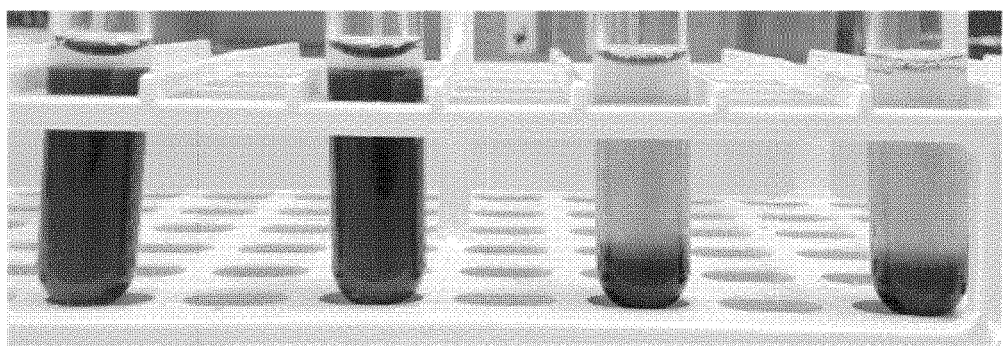

FIG. 15 shows comparative separation tests using (1) solvent (PBS) only (as control), (2) DMSO (i.e. no component (ii)), (3) DMSO+HES, and (4) DMSO+dextran 500.

EXAMPLES

Terms and Eequipment used in the Examples

"TotiCyte" refers to a combination of Dextran 500 and DMSO.

"TotiCyte 1×" refers to a TotiCyte composition based on PBS and containing 2.5% w/v Dextran 500 and 2.5% v/v DMSO.

"TotiCyte 5×" refers to a TotiCyte composition based on PBS and containing 7.5% w/v Dextran 500 and 7.5% v/v DMSO.

All experiments were performed using blood that had been mixed with CPDA as an anticoagulant unless otherwise stated. Also, unless stated otherwise, compositions added to blood cell-containing samples were based on phosphate-buffered saline (PBS).

An FACS (Fluorescence-activated cell sorting) machine (FACSCalibur 4CA, serial number E4378) was used to measure the amount of CD34 and/or CD45 cells in white blood cell fractions.

A Guave easyCyte 5 machine was used to measure the amount of TNC (total nucleated cell count) in white blood cell fractions.

As regards methods for cell separation, three different methods were adopted, namely Macopress, Syngen and manual. These methods were carried out as follows.

Macopress
1. Turn on Macopress. It is important to do this before step 11, as the Macopress cannot calibrate properly if a blood bag is already hanging on the machine.
2. Calculate how much blood+CPDA is in the blood bag.
3. Sterile dock the blood bag to the Macopress processing kit (line with white spike).
4. Cut off the clamp nearest to the buffy coat bag (the one with two tubes coming out of it, as opposed to one like the plasma bag), and close all other clamps.
5. Using the port on the collection bag line, add in an equal volume of 1× TotiCyte.
6. Agitate the bag both whilst and after completion of adding TotiCyte.
7. Use the syringe previously used to add the TotiCyte to remove as much air from the bag as possible (the Macopress buffy coat bag only holds 200 ml so make sure not to allow it to fill up with air before it can finish pressing).
8. Hang up the Macopress processing bag onto the Macopress and allow to separate for 30 minutes.
9. Using the arrows, choose program 4.
10. Follow the instructions given on the screen—insert the tubing into the clamps that are lit up (1, 3 and OPTI). Ensure there are no kinks in the line. Break the breakventile on the top of the bag and ensure the clamps on the buffy coat line are open, and those on other parts of the processing set are closed.
11. Press Enter to start the Macopress.
12. Press Escape once the Macopress has finished, to ensure that the machine does not seal the line at clamp 1.
13. Remove the bag and tubing from the Macopress.
14. Pull apart the seal between the two bags. Cut the tube of the buffy coat bag to allow the contents of the line to drain in. Heat seal this tube before proceeding to the next step.
15. Place the set snugly into a centrifuge bucket, aiming to ensure that the buffy coat bag will not crease up during the centrifugation step, and ensure that all clamps are closed.
16. Ensure the centrifuge is properly balanced, and then centrifuge at 500 g for 15 minutes.
17. Carefully remove the processing set from the centrifuge so as not to disturb the pellet.
18. Place the bag back onto the Macopress, this time putting the tubing into clamps 1 and 3 only.
19. Select program 3 (10 ml final volume), break the breakventile on top of the buffy coat bag and ensure all clamps on the extra tubing are closed before pressing Enter.
20. Remove the processing set from the Macopress and pull apart the seal between the two bags. This will leave a plasma bag and a buffy coat bag containing 10 ml.
21. Rub the buffy coat bag gently to remove all of the pellet from the ridges and then remove the buffy coat from the bag using a 20 ml syringe.
22. Measure exactly how much buffy coat there is (for working out the recovery).
23. TNC and viability can then be tested on the Guava easyCyte machine, and CD34 and CD45 cells and their viabilities on the FACS machine.

Syngen
1. Remove the blood from the Fenwal blood bag using a 50 ml syringe (or more than one if necessary). Record the volume removed.
2. Retain a small amount of this whole blood for use later on in working out TNC recovery.
3. Replace the blood back into the blood bag.
4. Measure out an equal volume of 1× TotiCyte.
5. Add this to the blood bag and mix well.
6. Remove the pin from the bottom of the cartridge and the cap from the blue filter.
7. Sterile dock the blood bag to the Syngen cartridge's central line.
8. Allow the blood/TotiCyte mix to flow into the cartridge.
9. Seal the line as close to the top of the cartridge as possible.
10. Invert the cartridge to further mix the sample, making sure to avoid getting any liquid into the 2 tubes at the side of the cartridge (tubes that go through to the other chambers) or into the blue filter.
11. Leave the sample to separate for 30 minutes.
12. Attach the cartridge to the Syngen processing module and switch it on.
13. Balance the centrifuge by using a Syngen cartridge filled with water attached to a processing module.
14. Spin the cartridge using program 1—this will go through 4 spin cycles which are each a different length and speed.
15. Remove the cartridge from the centrifuge, transferring the cartridge to the Syngen workstation and the processing module to the docking station (the module will now be displaying a P, indicating that the data needs to be processed).
16. Download the information from the module, entering in the information requested (centrifuge number, sample name, cartridge lot number and processing module lot number used).
17. The buffy coat chamber should contain 20 ml: remove this and measure exactly how much there is, as it can vary slightly.

18. Mix the buffy coat well then take a sample from it for viability analysis.
19. TNC and viability can then be tested on the Guava easyCyte machine, and CD34 and CD45 cells and their viabilities on the FACS machine.

Manual method
1. Calculate the volume of blood+CPDA.
2. Retain a small amount of this whole blood for use later on in working out TNC recovery.
3. Transfer this into a separation funnel attached to a retort stand. Ensure that the tap at the bottom is closed.
4. Add in an equal volume of 1× TotiCyte. Remove the lid to get rid of any excess air, and leave to separate for 30 minutes.
5. Place a falcon tube or dish underneath the funnel. Turn the tap to open the nozzle only slightly and allow the red fraction to flow out of the funnel.
6. Keep a close eye on the amount of red left: do not remove all of it as the interface will be lost if absolutely all of the red is removed.
7. Once sufficiently close to the interface, turn off the tap. Allow as much of the red to drip from the nozzle before removing the tube from underneath and replacing it with a new one.
8. Open the tap again to allow the white cell fraction to be aspirated.
9. Spin down the white cell fraction for 10 minutes at 500g and re-suspend in 10 ml of supernatant.
10. TNC and viability can then be tested on the Guava easyCyte machine, and CD34 and CD45 cells and their viabilities on the FACS machine.

EXAMPLE 1

General Cell Separation Method

Umbilical cord blood was collected into standard Baxter 250 ml (nominal) blood bags containing 35 ml of a citrate phosphate dextrose adenine (CPDA) anticoagulant solution.

A solution containing dextran and a further constituent selected from dimethyl sulphoxide (DMSO), dimethyl glycine (DMG), L-valine, L-proline, β-alanine, leucine, isoleucine and glycine, in phosphate-buffered saline (PBS), was prepared. This solution was added to a blood sample at a ratio of 1:1, this was then mixed thoroughly. Separation of the erythrocyte and nucleated cell fractions took place at room temperature within a time period of 15 or 30 minutes.

Figure 1:
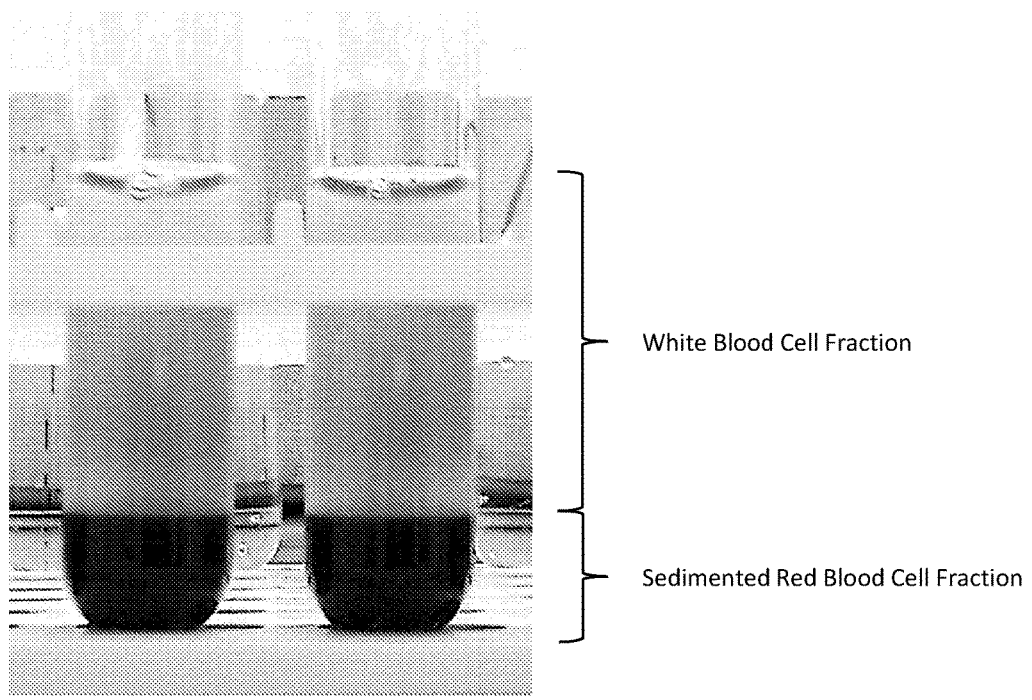

Separation of the cell fractions could be observed visually. FIG. 1 shows clear separation of the erythrocytes (bottom of test tube) from the nucleated cells (top of test tube). This image was taken 30 minutes after exposure to dextran (500 molecular weight (Mw)) at a final concentration of 2.5% w/v and DMSO at a final concentration of either 2% v/v (left image) or 2.5% v/v (right image).

Similar cell separation as described above was seen when dextran 500 Mw was replaced with dextran at a lower molecular weight of 70 Mw at a final concentration of between 3% and 5% w/v (data not shown). Similar cell separation was also seen when dextran 500 Mw was replaced with dextran 500 sulphate sodium at a final concentration of between 2.5% and 5% w/v (data not shown).

Blood samples that were exposed to dextran 70 Mw at a final concentration of 2.5% and DMG or L-valine at a final concentration of 2.5% w/v also showed a clear separation of erythrocytes and nucleated cells after 30 minutes (data not shown). By contrast, blood samples that were exposed to dextran 70 Mw at a final concentration of 2.5% w/v and L-proline, β-alanine, leucine, isoleucine or glycine at a final concentration of 2.5% w/v showed little if any separation of erythrocytes and nucleated cells after 30 minutes (data not shown here).

It was also observed that blood samples exposed to dextran 500 Mw at a final concentration of 2.5% w/v and DMSO at final concentration of 1% to 5% v/v showed a clear separation of erythrocytes and nucleated cells after 15 minutes and 30 minutes (FIG. 2).

Figure 2A:
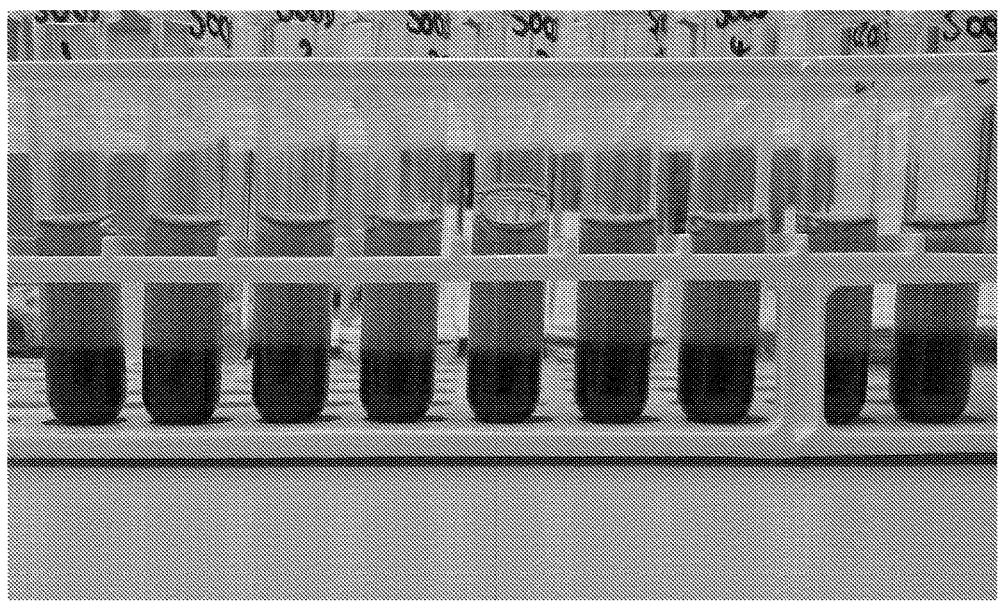
Figure 2B:
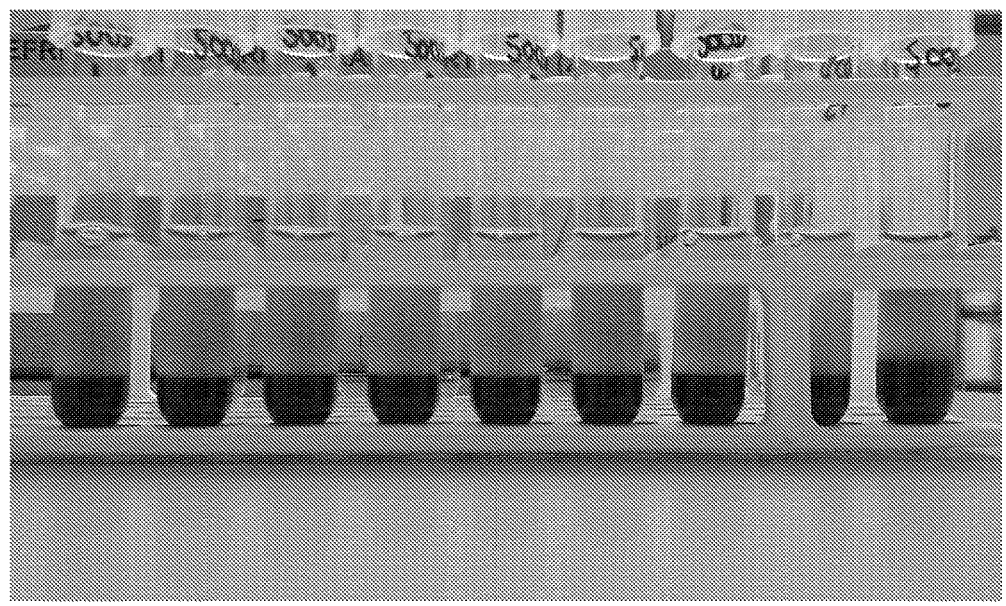

For the above experiments, substantial separation was often seen after 15 minutes of exposure, although further separation would be seen after between 15 minutes and 30 minutes of exposure. This is noticeable, for example, when the samples of FIG. 2a are compared against the samples of FIG. 2b.

EXAMPLE 2

Erythrocyte Volume Fraction (Haematocrit) Study

In this Example, the levels of erythrocyte volume fraction remaining in the nucleated cell fraction after cell separation were determined. Three tubes were prepared for the separation: (i) blood sample mixed at a ratio of 1:1 with PBS only (control), (ii) blood sample mixed at a ratio of 1:1 with a solution containing 500 Mw dextran at a concentration of 5% w/v in PBS (final concentration of dextran of 2.5% w/v), (iii) blood sample mixed at a ratio of 1:1 with a solution containing 500 Mw dextran at a concentration of 5% w/v and DMSO at a concentration of 5% v/v in PBS (final concentration of dextran of 2.5% w/v and of DMSO of 2.5% v/v). Samples were left to separate for 30 minutes at room temperature.

It was observed that the cell fractions in sample (iii) separated at a faster rate than in sample (ii) and, after 30 minutes, sample (iii) had developed a more compact erythrocyte fraction compared to sample (ii) (data not shown).

Nucleated cell fractions (100 μl) were transferred to a micropipette, and the ends were closed using plasticine. Micropipettes were then centrifuged for 2 minutes at 1500 rpm.

Figure 3:
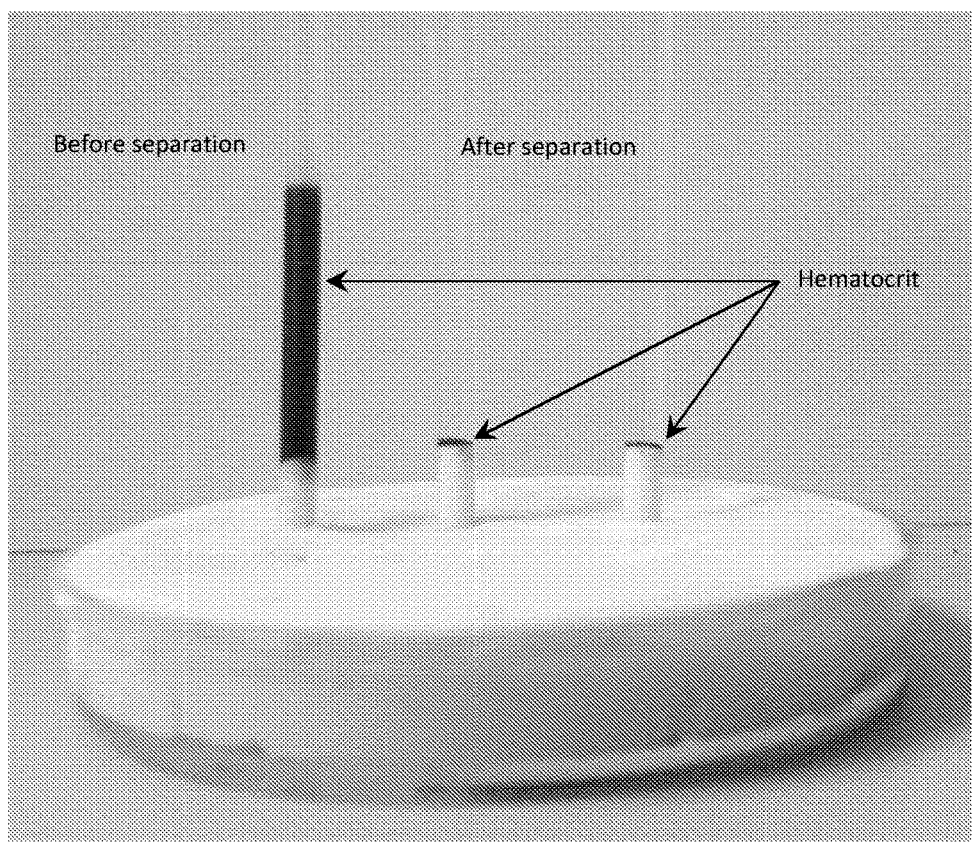

FIG. 3 shows the micropipettes after centrifugation. The control (left pipette in FIG. 3) shows a high packed erythrocyte volume within the white cell fraction. By contrast, samples (ii) (middle pipette) and (iii) (right pipette) showed a much reduced packed erythrocyte volume of approximately 1%.

EXAMPLE 3

Assessment of Cell Viability and the Presence of Hematopoietic Stem Cells (HSCs) using Flow Cytometry A blood sample was mixed at a ratio of 1:1 with a solution containing 500 Mw dextran at a concentration of 5% w/v and DMSO at a concentration of 5% v/v in PBS (final concentration of dextran of 2.5% w/v and of DMSO of 2.5% v/v). Samples were left to separate for 30 minutes at room temperature.

A sample of the resulting nucleated cell fraction was then analysed using flow cytometry. In particular, analysis was carried out using a "Stem Cell Enumeration Kit" obtained from Becton, Dickinson and Company. Analysis was carried out as per the Application Guide provided with the Kit and the templates used are based on a method featured in the Clinical and Laboratory Standards Institute H42-A2 approved guideline (Enumeration of Immunologically Defined Cell Populations by Flow Cytometry; Approved Guideline-Second Edition. Wayne, PA: Clinical and Laboratory Standards Institute; 2007. CLSI document H42-A2).

Figure 4:
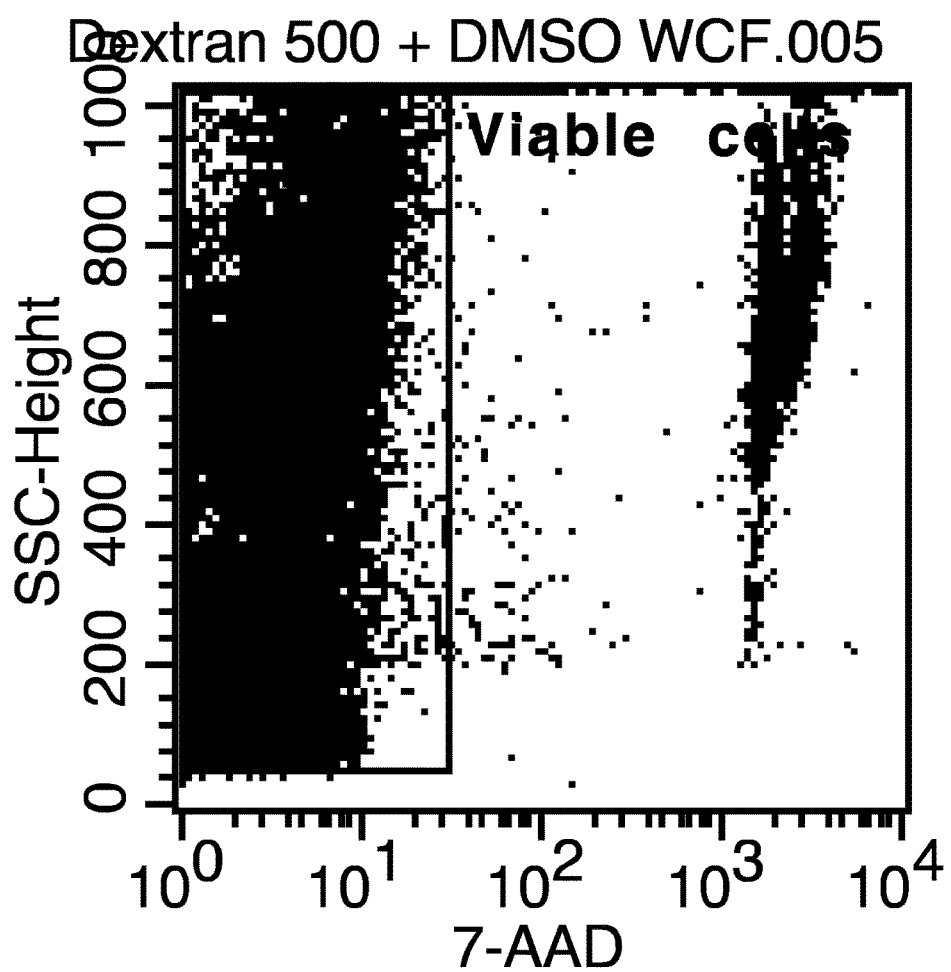

FIG. 4 shows a dot plot of 7-Aminoactinomycin D (7-AAD) fluorescence levels (x-axis) against side scatter (y-axis). 7-AAD is a fluorescent compound used to assess cell viability. It permeates the cell membranes of non-viable cells only, and so a low level of fluorescence (as represented by the rectangular gate on the dot plot) represents the cells that are viable. This dot plot shows that the majority of the total cell population are viable.

The flow cytometric analysis also showed that the cell separation method described above is an effective way of isolating a HSC population from a blood sample (data not shown).

EXAMPLE 4

Dextran 70 with Either DMSO or an Amino Acid

Figure 5:
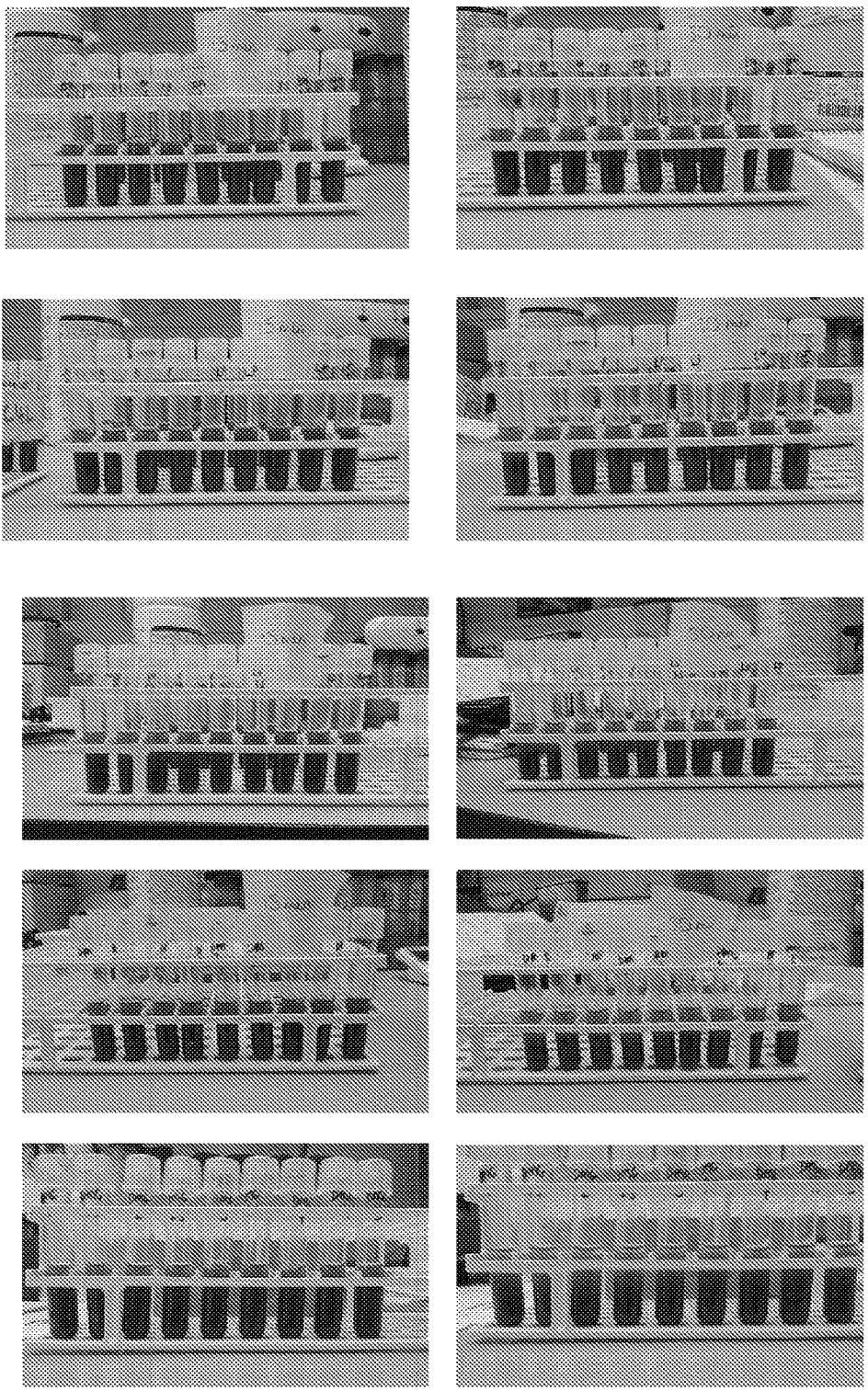

Whole blood samples were mixed with 1:1 with PBS compositions comprising 2.5% Dextran 70 plus DMSO, L-valine, L-proline, β-alanine, leucine, isoleucine, glycine and DMG. Each of the amino acids and the DMSO were tested at concentration levels of 1%, 1.5%, 2%, 2.5%, 3%, 3.5%, 4%, 4.5% and 5% in the PBS composition. After mixing, each sample was left for 30 minutes at room temperature. FIG. 5 shows images of the samples after 15 minutes and also after 30 minutes.

β-alanine did very little, even after 30 minutes. L-proline did very little after 30 minutes also. The tube with a 1% concentration separated out at a similar rate to the 2% tube in the L-valine experiment. In this regard, it may be worth noting that the results for some of the higher concentration amino acid solutions could have been affected by limitations in the solubility of the amino acid. L-valine performed better than DMG: the white cell fraction after 30 minutes was much clearer with the L-valine. None of isoleucine, leucine and glycine seemed to induce any sedimentation at all. FIG. 5 shows each of the substances described at the separation, except glycine, leucine and isoleucine are not shown due to their almost total inactivity—all of them separated out the blood no faster than blood mixed 1:1 with PBS. Below is a list of the order from best to worst of each substance at the separation:

DMSO>L-valine>DMG>L-proline>β-alanine>Leucine/isoleucine/glycine

EXAMPLE 5

Dextran Sizes and Types

Different molecular weights of Dextran were tested. In particular, Dextran 6, 40, 70 and 500 were compared. Stocks of 2-10% w/v (2%, 3%, 4%, 5%, 6%, 7%, 8%, 9% and 10%) of each molecular weight of Dextran were set up, to give concentrations of 1-5% once combined with the blood sample on a 1:1 basis by volume. The stocks all contained the same concentration of DMSO, namely 2.5% v/v.

Figure 6:
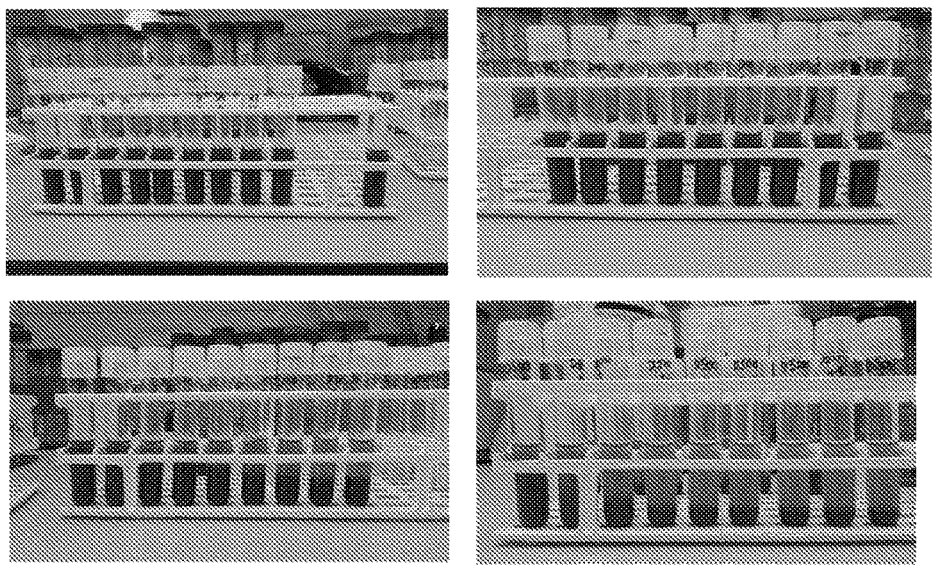

Dextran 6 and Dextran 40 didn't really separate out, either by 15 minutes or the full 30 minutes, as can be seen in FIG. 6. Dextran 70 did start to separate out quite well, with a clear gradient—the 5% concentration separated out much quicker and better than the lower concentrations. After 30 minutes, the Dextran 70 still had this clear gradient, with the higher concentrations separating over halfway down the tube. The Dextran 500 was clearly the best at the separation. The 3% tube had its red cell fraction almost completely compacted by the 15 minute mark, and after 30 minutes, all the tubes bar the 1% concentration were extremely well compacted: all of the tubes from 2.5% upwards looked essentially the same (some had slightly cloudier white cell fractions).

FIG. 6 shows images of the samples after 30 minutes. The Dextran 6 and 40 did not separate out any faster than the control (blood diluted with PBS). There is a clear gradient for the Dextran 70, but at lower concentrations it did not really separate out. The Dextran 500 separated the blood well and gave a clear white cell fraction.

EXAMPLE 6

Dextran 500 v Dextran Sulphate Sodium Salt

Dextran 500 (at 2.5% w/v) was mixed with DMSO at 2.5% v/v; the same was done with the Dextran sulphate sodium salt. lml of each composition was placed in a tube, and each tube had 1 ml of blood added, and was then left to separate for 30 minutes, as with most of the other experiments.

Figure 7:
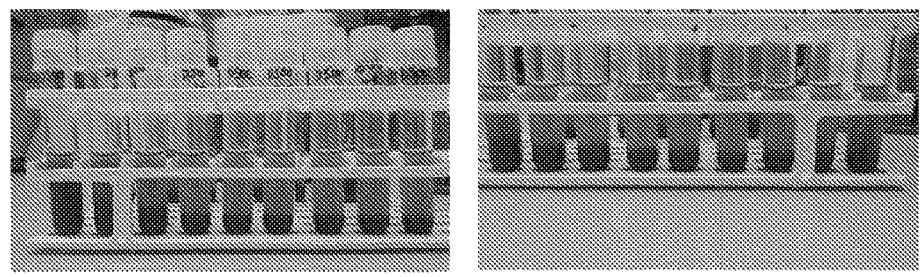
FIG. 7 shows a comparison of the separations of Dextran 500 v Dextran sulphate sodium salt after 30 minutes.

Dextran 500 sulphate sodium salt separated the blood out relatively well, but not quite as well as the Dextran 500/DMSO combination, as seen in FIG. 7. The compactness was very similar, but the white cell fraction was much cloudier in the Dextran salt, with many red cells visibly floating around just above the red cell fraction, as can be seen in FIG. 4 below. Thus, while both are effective, the Dextran 500 provided a slightly clearer white fraction.

Figure 8:
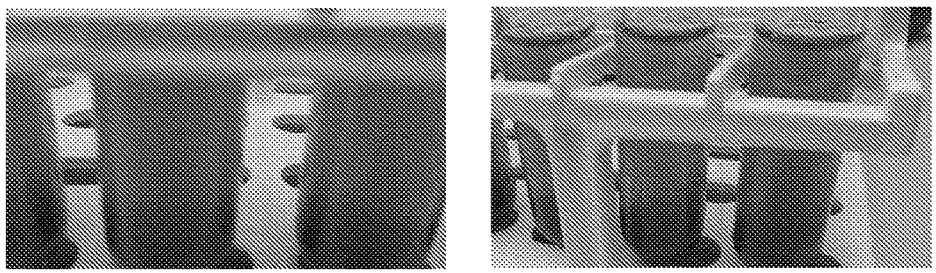
FIG. 8 shows close ups of Dextran 500 and Dextran 500 sulphate sodium salt separations. These close ups were taken at the 30 minute mark to demonstrate the extra cloudiness of the Dextran sulphate sodium salt separation.

FIG. 8 shows close ups of Dextran 500 and Dextran 500 sulphate sodium salt separations resulting from following the protocol described above in this Example. These close ups were taken at the 30 minute mark to demonstrate the extra cloudiness of the Dextran sulphate sodium salt separation.

At this point it is worth noting that while all aspects of the invention are believed to offer advantages over the prior art, the Dextran 500/DMSO combination, especially when used in the form of a composition obtainable by mixing equal volumes of (i) 2.5% w/v Dextran 500 in PBS with (ii) 2.5% v/v DMSO in PBS), stands out from the experiments discussed in this Example and preceding Examples as particularly advantageous.

EXAMPLE 7

Haematocrit Experiment

The level of haematocrit remaining in the white cell fraction was investigated. Three tubes were prepared for the separation, each containing a 1:1 mixture of blood:PBS-based composition (the first composition was PBS alone, as a control; the second composition had 5% w/v Dextran 500 mixed 1:1 with PBS (to give 2.5% w/v); the third composition was TotiCyte 1×) and left for 30 minutes at room temperature to ensure maximum separation. The sample with TotiCyte 1× separated slightly faster than the one with just Dextran. Both remained relatively cloudy until after 30 minutes of separation, at which point the TotiCyte had developed a more compact red cell fraction. 100 ul of the white cell fraction was transferred to a micropipette, and the ends closed up using plasticine. The micropipettes were then centrifuged for 2 minutes at 1500 rpm. Both the Dextran only and the TotiCyte samples had around 1% haematocrit and seemed much more compact than the control. To the naked eye there were no differences in the amount of haematocrit in the Dextran only and the TotiCyte tubes, as can be seen in FIG. 9.

In addition, samples were tested for haematocrit levels both using the Macopress machine and manually. The Macopress produced fairly consistent results as the machine was set to only collect a certain level of haematocrit (the Macopress stops the press action when a given level of red cells travel through the sensor, so in theory the amount that it leaves should always be the same). Values above 1% residual haematocrit only arose for runs where the sensitivity of the sensor had been altered. It was more difficult to get a constant level of haematocrit with the manual method, as to some extent, how much red to take off without taking the interface is subjective.

EXAMPLE 8

Varying Concentrations of Dextran 70 and 500

With the aim of determining optimum concentrations of DMSO and Dextran, varying concentrations of Dextran 70 and 500 (1, 1.5, 2, 2.5, 3, 3.5, 4, 4.5, and 5% w/v) were mixed with 2.5% v/v DMSO and blood (as usual, equal volumes of the Dextran and DMSO solutions were combined, and then a volume of blood added corresponding to that of the combined Dextran and DMSO solution), and left to separate for 30 minutes. The samples derived from the Dextran 500 components with 2.5%-4.5% started to separate out quite well even after 5 minutes. After 5 minutes, the Dextran 70 appeared not to have changed. FIG. 10 shows images of the samples after 5 minutes.

After 15 minutes, the majority of the separation had finished for each of the samples with Dextran 500 (except 1%), although after 30 minutes the fractions did become more compacted and clearer. The Dextran 70 had not done much after 15 minutes, although the tube at a concentration of 5% Dextran 70 had started to make some headway on the compaction; FIG. 11 shows images of the samples after 15 minutes. After 30 minutes, though, there was a very clear gradient: the first four tubes (1, 1.5, 2 and 2.5%) had not really separated out, but the tubes at 3-5% had separated well, although were not as compact or have such clear white cell fractions as the samples with corresponding concentrations of Dextran 500; FIG. 12 shows images of the samples after 30 minutes.

The second half of this experiment involved changing the concentration of DMSO, whilst keeping the Dextran concentration constant. To this end, 2.5% w/v Dextran 500 was mixed with varying concentrations of DMSO solutions (1, 1.5, 2, 2.5, 3, 3.5, 4, 4.5, and 5% v/v). For comparison, equivalent tests were also done using a 1.5% w/v Dextran 70 solution and also a 3% w/v Dextran 70 solution (in place of the Dextran 500). After 15 minutes, the Dextran 500/DMSO tubes had all compacted the red cell fraction down quite well—to about ⅓ of the tube. The 5% tube was the only one not to be quite so compacted at this stage. However, after 30 minutes all tubes had compacted even further and had much clearer white cell fractions. The sample derived from the 1.5% Dextran 70 solution did not appear to work any faster than blood mixed with PBS that had been left to separate (control). There was little/no change in the clarity and compactness of the Dextran 70 concentrations even after 30 minutes. FIGS. 13 and 14 show images of the samples. The bottom two images in FIG. 14 are of the sample derived from the 3% Dextran 70 solution. This made much more difference on the separation, and at 30 minutes, defined white and red cell fractions had developed. The red cell fraction was not as well compacted as it was with Dextran 500, but it was much clearer than in the sample derived from the 1.5% Dextran 70 solution.

EXAMPLE 9

Actual Numbers of Cells Recovered in the White Cell Fractions

CD34 and CD45 Count

Separations were carried out on two different blood samples. For each sample, a separation was done using (a) TotiCyte 1×, and (b) a 2.5% w/v Dextran 500 solution. The 2.5% Dextran solution was mixed with 1ml of blood such that the final concentration of Dextran in the sample was the same as in the TotiCyte replicate (in which both the DMSO and Dextran 500 components have a final concentration of 1.25% [v/v and w/w, respectively]). After 30 minutes or so at room temperature, once the separation had progressed as far as it would go, the white cell fraction was removed and transferred to another tube. 100 ul of this was run on the FACS machine to test for CD34 and CD45 cells. The effect of introducing the DMSO (in the TotiCyte sample) on the quantity of cells recovered was as follows:

On average, separation using TotiCyte recovered 29% more CD34 cells than when the Dextran only solution was used On average, separation using TotiCyte recovered 7% more CD45 cells than when the Dextran only solution was used In terms of cell viability %, the proportion of the recovered cells that were viable was slightly lower when the TotiCyte composition was used as compared to the Dextran only solution, but this was generally more than offset by a greater number of cells being recovered when the TotiCyte composition was used (meaning that there were significantly more viable cells recovered using the TotiCyte composition).

Further Testing of TNC (Total Nucleated Cell) Count & C34 Count

Corresponding testing was also done to confirm the effectiveness of the TotiCyte 1× across a larger sample size. In addition, corresponding testing was also done to confirm the viability of using TotiCyte 5×. The results are summarised in the following table.

| Composition used | Processing method | TNC recovery % | CD34 recovery % |
| --- | --- | --- | --- |
| TotiCyte 1X | Macopress | 97* | 79* |
|  | Manual | 99 | 87 |
|  | Syngen | 78* | 90 |
|  | Any of the above | 91* | 81* |
| TotiCyte 5X | Macopress | 66 | 68 |

*average values taken from 9 samples in the case of the Macopress method and from 2 samples in the case of the Syngen method The testing showed that TotiCyte 1× enabled consistently high TNC recovery rates, regardless of the choice of method (i.e. using a manual method, the Syngen system or the Macopress). CD34 cell recovery was also high. The viability of using the more concentrated TotiCyte 5× composition was confirmed, although the Toticyte 1× composition generally provided the highest recovery rates.

Post-thaw Analysis

Further testing was done to compare the effects of the proposed separation methods following downstream addition of DMSO to known cryoprotective levels, freezing, and then thawing. In each case, the addition of DMSO prior to freezing was done following the approach described in Example 11 below, and the same freeze thaw process was used. When DMSO was added prior to freezing, it was added at 4° C., and was added slowly so as not to shock the cells; the samples were frozen in a validated passive freeze box with a fluid-filled blood bag on top (how the boxes were validated); samples were thawed quickly at 37° C. by swirling and gently inverting the tube, before being moved into wet ice as soon as the mixture became slushy; the blood was sampled quickly after complete thawing to ensure maximum retention of viability. The results are summarised in the table below, alongside corresponding results for whole blood samples. For the washing step, thawed cell suspension was centrifuged at 500 g for 10 min; the supernatant was discarded and cell pellet gently resuspended in cold PBS; the cell suspension was centrifuged again at 500 g for 10 min and the pellet resuspended in cold PBS to the volume desired.

| Composition used (sample size) | Sample washed prior to cell count? | Average TNC recovery % | Average CD34 recovery % |
|---|---|---|---|
| N/A - whole blood used (5) | No | 128 | 86 |
| Toticyte 1X (5) | | 107 | 81 |
| TotiCyte 5X (3) | | 79 | 91 |
| N/A - whole blood used (5) | Yes | 58 | 71 |
| Toticyte 1X (5) | | 66 | 66 |
| TotiCyte 5X (3) | | 34 | 27 |

The samples treated with TotiCyte 1× and TotiCyte 5× both provided good post thaw recovery levels, with the TotiCyte 1× proving particularly effective. There was a significant difference between the viabilities of each whole blood and its corresponding TotiCyte 1× and 5× replicates. For the most part, it was found during the course of these experiments that whole blood does not always survive the thawing process particularly well. Thus, notwithstanding inevitable variations between different blood samples, it was found that while more cells were generally recovered from the whole blood cell samples, recovery figures were generally comparable to the TotiCyte 1× replicate once viability was taken into account. Indeed, the average TNC count (66%) for the samples treated with TotiCyte 1× and subjected to washing was even higher than the corresponding average TNC count (58%) for whole blood. Similarly, the average CD34 count (91%) for the samples treated with TotiCyte 5× and not subjected to washing was even higher than the corresponding CD34 count (86%) for whole blood. (It is worth noting in connection with the above results that while recovery levels of >100% are of course not possible, levels >100% can nonetheless be recorded in testing, due e.g. to variation within blood samples.)

EXAMPLE 10

Different Anticoagulants

A blood sample was processed using TotiCyte 1×, but with half containing CPD and the other half containing CPDA. Both were processed manually in separation funnels, with the red cell fraction being siphoned off first before collection of the white cell fraction. Both were tested on the FACS machine and Guava easyCyte for CD34/CD45 cells and TNC, respectively. The results are as follows.

| Anticoagulant | Average TNC recovery % (sample size = 2) | Average CD34 recovery % (sample size = 2) |
|---|---|---|
| CPD | 80 | 57 |
| CPDA | 79 | 81 |

The TNC recovery between the two anticoagulants is similar. Testing of CD45 recovery % showed that 87% were recovered with the CPDA fraction, compared to 70% CD45 with the CPD fraction (data not shown). Both anticoagulants are suitable for use according to the invention, though there may be instances where CPDA is preferred.

EXAMPLE 11

Priming a Cell Fraction for Freezing to Enhance Post Thaw Recovery

The following method was followed to test the effect on post thaw cell recovery of carrying out the priming method of the present invention prior to contacting the cell fraction with a cryoprotectant and freezing then thawing it.

1. Trypsinise was used to remove the cells from the flask.
2. The cells were spun down to remove the trypsin.
3. The cells were then resuspended in 10 ml DMEM.
4. TNC and CD45/CD34 cell counts were measured (in order to determine post thaw cell recovery).
5. 0.5 ml was aliquoted out into each of eight 2 ml cryovials.
6. A further 0.5 ml DMEM was added to the first two tubes, 0.5 ml of TotiCyte 1× to each of the next two, 0.1 ml of TotiCyte 5× to each of the next two, and 0.5 ml of 2.5% w/v Dextran 500 to the final two tubes. The samples were then mixed well.
7. The samples were then left for 45 minutes at room temperature.
8. DMSO was added to one of each pair of tubes (i.e. one of each of the four types) up to 7.5%. To the other four tubes, a combination of DMSO and FCS (fetal calf serum) was added.
9. The cell samples were transferred to a Mr Frosty freezing receptacle.
10. The bottom compartment was filled with methanol, and the whole container placed in a −80° C. freezer for at least one night.
11. The container was removed from the freezer and thawed quickly.
12. Part of the fraction was removed to another tube for a retest without washing.
13. To the cells remaining after the removal of this small aliquot, half the volume of warmed DMEM was added dropwise, with the tube being swirled gently all the time.
14. The samples were then centrifuged for 10 minutes at 500 g.
15. The supernatant was removed and resuspended in 0.5 ml DMEM.
16. The samples were then retested for cell recovery.

The above protocol was followed, including leaving the samples in the freezer for ⅔ days before thawing. The TNC recovery (as measured on Guava PCA) results are set out below.

| Composition used | Cryopreservant | Pre-freeze viability % | Post-thaw viability % |
|---|---|---|---|
| DMEM | DMSO | 90.2 | 77.67 |
| DMEM | DMSO/FCS | 90.2 | 69.75 |
| TotiCyte 1X | DMSO | 90.2 | 87.13 |
| TotiCyte 1X | DMSO/FCS | 90.2 | 91.03 |
| TotiCyte 5X | DMSO | 90.2 | 73.9 |
| TotiCyte 5X | DMSO/FCS | 90.2 | 76.1 |
| Dextran only | DMSO | 90.2 | 82.9 |
| Dextran only | DMSO/FCS | 90.2 | 81.6 |

Both Dextran and DMSO had a priming effect on cells, as the TotiCyte and Dextran cell recoveries were both significantly better than the control. After a wash step, the TotiCyte 1× appeared to be the best at maintaining TNC post-thaw, as well as retaining 85%+viability, followed by the Dextran alone, then 5× TotiCyte.

EXAMPLE 12

Further Comparative Testing

Further blood separations were carried out using the following compositions:
Blood+equal volume of PBS as control (test 1)
Blood+equal volume of PBS with 2.5% v/v DMSO, such that the concentration of DMSO following mixing with the blood sample was 1.25% v/v (test 2)
Blood+equal volume of PBS with 2.5% w/v HES (hydroxyethyl starch) and 2.5% v/v DMSO (test 3)
Blood+equal volume of TotiCyte 1×, i.e. PBS with 2.5% w/v dextran 500 and 2.5% v/v DMSO (test 4).

Images of the separation achieved in these tests appear in FIG. 15. As is evident, the DMSO-only composition used in test 2 performed no better than the control (test 1)—neither achieving any separation over the course of the test (60 minutes). Comparable separation was seen in tests 3 and 4, confirming HES as a viable alternative to dextran.

The invention claimed is:

1. A method for separating cells, said method comprising:
   (a) contacting a blood cell-containing sample containing erythrocyte blood cells with:
       (i) a macromolecular erythrocyte sedimentation enhancer, and
       (ii) dimethyl sulphoxide (DMSO), dimethylglycine (DMG) and/or valine;
   (b) allowing said sample to partition into a sedimented phase and a supernatant phase; and
   (c) recovering non-erythrocyte blood cells from said supernatant phase;
   wherein in step (a), when the sample is contacted with components (i) and (ii), the resulting mixture comprises component (i) at a concentration of 0.01 to 10% w/v, and component (ii) at a concentration of 0.01 to 10% w/v.

2. A method according to claim 1, said method comprising:
   (a) contacting the blood cell-containing sample with a composition comprising:
       (i) dextran, and
       (ii) DMSO, DMG or valine;
   (b) allowing said sample to partition into a sedimented phase and a supernatant phase; and
   (c) recovering non-erythrocyte blood cells from said supernatant phase.

3. A method according to claim 1, wherein step (a) comprises contacting the blood cell-containing sample with a composition comprising components (i) and (ii), and the blood cell containing sample and the composition are mixed at a volume ratio of 10:1 to 1:10.

4. A method according to claim 1, wherein step (a) comprises contacting the blood cell-containing sample with either:
   a composition comprising 0.5-10% w/v of component (i) and 0.5-10% v/v of component (ii);
   or
   two or more separate compositions comprising component (i) and/or (ii), which, if combined, would give a composition comprising 0.5-10% w/v of component (i) and 0.5-10% v/v of component (ii).

5. A method according to claim 1, wherein the blood cell-containing sample is selected from peripheral blood, umbilical cord blood or bone marrow.

6. A method according to claim 1, wherein the blood cell-containing sample is taken from a human.

7. A method according to claim 1, wherein said sample is allowed to partition into a sedimented phase and a supernatant phase in step (b) for 10 to 60 minutes.

8. A method according to claim 1, wherein, once the blood cell-containing sample has been contacted with components (i) and (ii), the concentration of component (i) is 0.25 to 5% w/v, and the concentration of component (ii) is 0.25 to 5% v/v.

9. A method according to claim 1, wherein component (i) is dextran and component (ii) is DMSO.

10. A method according to claim 1, wherein component (i) is dextran having a molecular weight of at least 50 kDa.

11. A method according to claim 1, wherein component (i) is dextran 500 and component (ii) is DMSO.

12. A method according to claim 1, wherein the supernatant phase resulting from step (b) has a hematocrit of less than 1%.

13. A method according to claim 1, wherein the method is for increasing the proportion of viable white blood cells recovered following a subsequent cryopreservation.

14. A method for preparing non-erythrocyte blood cells for cryopreservation, which method comprises (a) a method as defined in claim 1, and (b) adding a cryoprotectant to the thus obtained non-erythrocyte blood cells.

15. A method for the cryopreservation of non-erythrocyte blood cells, which method comprises (a) a method as defined in claim 1, (b) adding a cryoprotectant to the thus obtained non-erythrocyte blood cells, and (c) cryopreserving the non-erythrocyte blood cells.

16. A method for the cryopreservation and subsequent recovery of non-erythrocyte blood cells, which method comprises (a) a method as defined in claim 1, (b) adding a cryoprotectant to the thus obtained non-erythrocyte blood cells, (c) cryopreserving the non-erythrocyte blood cells, and (d) thawing the non-erythrocyte blood cells.

17. A method according to claim 14, wherein the cryoprotectant comprises DMSO.

18. A method according to claim 1, wherein component (i) is polybrene, protamine sulphate, polyethylene glycol (PEG), hydroxyethyl starch (HES), polyvinyl pyrrolidone (PVP), or dextran.

19. A method according to claim 1, wherein component (i) is hydroxyethyl starch (HES) or dextran.

20. A method according to claim 1, wherein component (i) is a polysaccharide.

21. A method according to claim 3, wherein the volume ratio is 5:1 to 1:5.

22. A method according to claim 3, wherein the volume ratio is 2:1 to 1:2.

23. A method according to claim 1, wherein the separation method does not include the use of any antibodies.

24. A method according to claim 3, wherein the composition comprising components (i) and (ii) does not contain any antibodies.

25. A method for separating cells, said method comprising:
- (a) contacting a blood cell-containing sample containing erythrocyte blood cells with:
  - (i) a macromolecular erythrocyte sedimentation enhancer, and
  - (ii) DMSO, DMG and/or valine;
- (b) allowing said sample to partition into a sedimented phase and a supernatant phase; and
- (c) recovering non-erythrocyte blood cells from said sedimented phase; wherein in step (a), when the sample is contacted with components (i) and (ii), the resulting mixture comprises component (i) at a concentration of 0.01 to 10% w/v, and component (ii) at a concentration of 0.01 to 10% w/v.

26. A method for separating cells, said method comprising:
- (a) contacting a blood cell-containing sample containing erythrocyte blood cells with:
  - (i) a macromolecular erythrocyte sedimentation enhancer, and
  - (ii) DMSO, DMG and/or valine;
- (b) allowing said sample to partition into a sedimented phase and a supernatant phase; and
- (c) recovering erythrocyte blood cells from said sedimented phase; wherein in step (a), when the sample is contacted with components (i) and (ii), the resulting mixture comprises component (i) at a concentration of 0.01 to 10% w/v, and component (ii) at a concentration of 0.01 to 10% w/v.

* * * * *

UNITED STATES PATENT AND TRADEMARK OFFICE
CERTIFICATE OF CORRECTION

PATENT NO.         : 10,190,091 B2
APPLICATION NO.    : 14/784492
DATED              : January 29, 2019
INVENTOR(S)        : Jeffrey Drew It is certified that error appears in the above-identified patent and that said Letters Patent is hereby corrected as shown below:

In the Claims

Column 25, Line 57: Delete "w/v" and insert in its place --v/v--.

Column 28, Line 3: Delete "w/v" and insert in its place --v/v--.

Column 28, Line 18: Delete "w/v" and insert in its place --v/v--.

Signed and Sealed this
Twenty-third Day of April, 2019

Andrei Iancu
*Director of the United States Patent and Trademark Office*